(12) United States Patent
Bigham et al.

(10) Patent No.: US 6,884,801 B1
(45) Date of Patent: Apr. 26, 2005

(54) IMIDAZOLINE DERIVATIVES AS ALPHA-1A ADRENOCEPTOR LIGANDS

(75) Inventors: Eric Cleveland Bigham, Durham, NC (US); Michael Joseph Bishop, Durham, NC (US); David Harold Drewry, Durham, NC (US); Deanna Trojan Garrison, Durham, NC (US); Stephen Joseph Hodson, Durham, NC (US); Frank Navas, III, Durham, NC (US); Jason D. Speake, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/019,976

(22) PCT Filed: Apr. 28, 2000

(86) PCT No.: PCT/EP00/03848

§ 371 (c)(1),
(2), (4) Date: Oct. 23, 2001

(87) PCT Pub. No.: WO00/66563

PCT Pub. Date: Nov. 9, 2000

(30) Foreign Application Priority Data

Apr. 30, 1999 (GB) .............................. 9910110

(51) Int. Cl.⁷ ............... A61K 31/5375; A61K 31/4164; C07D 403/02; C07D 413/10
(52) U.S. Cl. .................... 514/235.8; 544/106; 544/139; 546/184; 546/210; 548/314.7; 548/349.1; 548/351.1; 514/326; 514/399
(58) Field of Search .......................... 548/314.7, 349.1, 548/351.1; 514/399, 235.8, 326; 546/210; 544/106, 139, 136

(56) References Cited

U.S. PATENT DOCUMENTS

| 3,754,002 A | 8/1973 | Brown et al. |
| 4,506,074 A | 3/1985 | Huff et al. |

FOREIGN PATENT DOCUMENTS

| WO | 0 887 346 | 12/1998 |

OTHER PUBLICATIONS

Hodson et al (2002): J. Med. Chem, vol 45, 2229–2239.*

Saari, Walfred S., J. Med. Chem., (1983), 26, 1769–72.

* cited by examiner

*Primary Examiner*—Golam M M Shameem
(74) *Attorney, Agent, or Firm*—Robert H. Brink

(57) ABSTRACT

Compound of formula (I) or a pharmaceutically acceptable salt or solvate thereof are disclosed. Such compounds are useful in the treatment of Alpha-1A mediated diseases or conditions such as urinary incontinence.

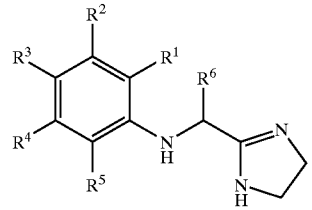

(I)

21 Claims, No Drawings

IMIDAZOLINE DERIVATIVES AS ALPHA-1A ADRENOCEPTOR LIGANDS

This application is filed pursuant to 35 U.S.C. §371 as a United States National Phase Application of International Application No. PCT/EP00/03848 filed 28 Apr. 2000, which claims priority from GB 9910110.7 dated 30 Apr. 1999 in the United Kingdom.

The present invention relates to certain phenylaminoalkyl-2-imidazoline compounds and their use in the treatment of various diseases and conditions such as urinary incontinence.

Alpha-1A adrenoceptors ("alpha-1A") are specific neuroreceptor proteins located in the peripheral and central nervous systems and on tissues throughout the body. The receptors are important switches for controlling many physiological functions and represent important targets for drug development. Certain alpha-1A agonists are known and are indicated to be useful in treating various disease states including urinary incontinence, nasal congestion, priapism, depression, anxiety, dementia, senility, Alzheimer's, deficiencies in attentiveness and cognition, and eating disorders such as obesity, bulimia, and anorexia. See for example, European patent application EP 0,887,346 A2 (Cournoyer et al.) which discloses certain phenyl and aminophenyl alkylsulfonamide and urea derivatives said to be alpha-1A agonists. See also international patent publication WO 96/38143 (Craig et al.).

There are many examples of known imidazoline derivatives. See, for example, the following U.S. patents: U.S. Pat. No. 4,254,133 (Kristinsson and Traber) discloses certain phenylaminoalkyl-2-imidazoline compounds said to be useful for controlling ectoparasites. U.S. Pat. No. 3,754,002 (Brown) discloses certain substituted imidazolinylmethyl anthranilates said to stimulate the alpha-adrenergic nervous system of mammals. U.S. Pat. No. 4,414,223 (Copp et al.) discloses certain anilinomethylimidazolines said to be useful as pesticides. U.S. Pat. No. 4,483,858 (Saari) discloses certain imidazoline derivatives said to have antihypertensive activity. U.S. Pat. No. 4,506,074 (Huff et al.) discloses certain imidazoline derivatives said to be selective alpha-2 adrenergic receptor antagonists and alpha-1 adrenergic receptor agonists. See also the following publications. "Alpha-Adrenergic Activities of Some Substituted 2-(Aminomethyl)imidazolines," by Walfred S. Saari et al., J. Med. Chem., vol. 26 (no. 12), pp. 1769–1772, (1983).

Briefly, in one aspect, the present invention discloses compounds of formula (1) and pharmaceutically acceptable salts and solvates thereof.

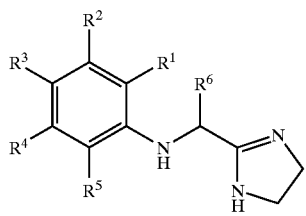

(I)

where $R^2$, $R^3$, $R^4$, and $R^5$ are independently H, halogen, —OH, —$C_{1-3}$alkyl, —$C_{1-3}$alkoxy, —$SC_{1-2}$alkyl, or —$CF_3$, with the proviso that at least 2 of $R^2$, $R^3$, $R^4$, and $R^5$ are H;

$R^6$ is H or —$CH_3$;

$R^1$ is —$S(O)_nR^7$ where, n is 1 or 2, —$S(O)_2NHR^8$, —$C(O)R^9$, —$NR^{14}R^{15}$, —$C(R^{17})$=$NOR^{16}$,

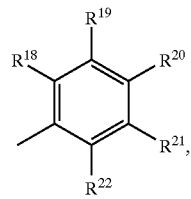

or a 5, 6, or 7 membered heteroalkyl or heteroaryl group optionally substituted with 1 or two groups selected from the group consisting of the following substituents for carbon: $C_{1-3}$alkyl, —$CH_2CF_3$, —$CF_3$, F, Cl, $C_{1-2}$alkoxy, $C_{1-2}$thioalkyl, and the following substituents for nitrogen: $C_{1-3}$alkyl and —$CH_2C_{1-2}$fluoroalkyl;

$R^7$ is $C_{1-3}$alkyl or $C_{1-2}$fluoroalkyl;

$R^8$ is $C_{1-3}$alkyl or —$CH_2C_{1-2}$fluoroalkyl;

$R^9$ is $C_{1-3}$alkyl optionally substituted with 1–3 fluorine atoms, —$NR^{10}R^{11}$, —$NHNR^{12}R^{13}$, —$CH_2SO_2CH_3$,

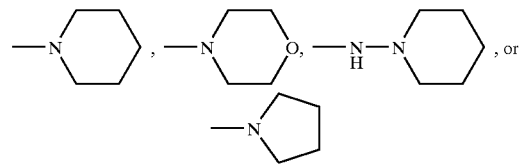

$R^{10}$ is H or $C_{1-2}$alkyl;

$R^{11}$ is H, cyclopropyl, cyclopropylmethyl, $C_{3-6}$alkenyl with the proviso that any unsaturation is not adjacent to the depicted nitrogen, or $C_{1-6}$alkyl optionally substituted with hydroxy, $C_{1-3}$alkoxy, or 1–3 fluorine atoms with the proviso that the carbon atom in $R^{11}$ that is bonded to the depicted nitrogen is not bonded to either a fluorine or an oxygen;

$R^{12}$ is H or $C_{1-2}$alkyl;

$R^{13}$ is H, $C_{3-5}$cycloalkyl, cyclopropylmethyl, —$SO_2CH_3$, —$C(O)CH_3$, $C_{3-6}$alkenyl with the proviso that any unsaturation is not adjacent to the depicted nitrogen, or $C_{1-6}$alkyl optionally substituted with hydroxy, $C_{1-3}$alkoxy, or 1–3 fluorine atoms with the proviso that the carbon atom in $R^{13}$ that is bonded to the depicted nitrogen is not bonded to either a fluorine or an oxygen;

$R^{14}$ is H or $C_{1-2}$alkyl;

$R^{15}$ is $C_{3-5}$cycloalkyl, cyclopropylmethyl, $C_{3-6}$alkenyl with the proviso that any unsaturation is not adjacent to the depicted nitrogen, or $C_{1-6}$alkyl optionally substituted with hydroxy, $C_{1-3}$alkoxy, or 1–3 fluorine atoms with the proviso that the carbon atom in $R^{15}$ that is bonded to the depicted nitrogen is not bonded to either a fluorine or an oxygen;

$R^{16}$ is $C_{1-2}$alkyl;

$R^{17}$ is H or $C_{1-3}$alkyl;

$R^{20}$ is H; and $R^{18}$, $R^{19}$, $R^{21}$, and $R^{22}$ are independently H, halogen, hydroxy, $C_{1-3}$alkyl, $C_{1-3}$alkoxy, —$SC_{1-2}$alkyl, or —$CF_3$ with the proviso that at least one of $R^{18}$, $R^{19}$, $R^{21}$, or $R^{22}$ is other than H. Preferably, the compounds of this invention are alpha-1A agonists.

In another aspect, the present invention discloses a method for prevention or treatment of an alpha-1A mediated disease or condition comprising administration of a therapeutically effective amount of a compound of this invention.

As used herein, "a compound of the invention" means a compound of formula (I) or a pharmaceutically acceptable salt, or solvate thereof. Alpha-1A agonist mediated diseases or conditions include urinary incontinence, nasal congestion, priapism, depression, anxiety, dementia, senility, Alzheimer's, deficiencies in attentiveness and cognition, and eating disorders such as obesity, bulimia, and anorexia. In particular, the compounds of this invention are useful in the treatment and prevention of urinary incontinence.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of an Alpha-1A mediated disease or condition.

Preferably, $R^2$, $R^3$, and $R^5$ are H or F.

Preferably $R^4$=H, F, Cl, —OCH$_3$, or —CH$_3$. Most preferably, $R^4$ is H, F, or Cl.

Preferably, $R^6$ is H.

Preferably, when $R^1$ is said 5, 6, or 7 membered heteroalkyl or heteroaryl group, $R^1$ is an imidazolidinyl, azepinyl, piperidyl, pyrrolidinyl, pyridyl, pyridazinyl, pyrimidinyl, pyrazinyl, pyrrolyl, pyrazolyl, imidazolyl, pyranyl, furyl, thienyl, oxazolyl, isoxazolyl, oxadiazolyl, thiazolyl, thiadiazolyl, triazolyl, or tetrazolyl group. Preferably, said 5, 6, or 7 membered heteroalkyl or heteroaryl group is unsubstituted or monosubstituted. Most preferably, said 5, 6, or 7 membered heteroalkyl or heteroaryl group is:

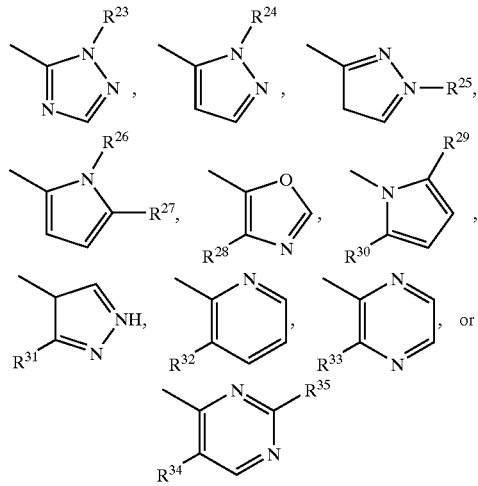

where $R^{23}$ is H, $C_{1-3}$alkyl, or 2,2,2-trifluoroethyl, $R^{24}$ is H, $C_{1-3}$alkyl, or 2,2,2-trifluoroethyl, $R^{25}$ is H, methyl, or ethyl, $R^{26}$ is H, methyl, or ethyl, $R^{27}$ is H or methyl, $R^{28}$ is H or methyl, $R^{29}$ is H or methyl, $R^{30}$ is H or methyl, $R^{31}$ is H or methyl, $R^{32}$ is H, methyl, ethyl, or trifluoromethyl, $R^{33}$ is H or methyl, $R^{34}$ is H or methyl, $R^{35}$ is H, methyl, amino, or hydroxy (or a tautomeric form). Most preferably, $R^{23}$ is isopropyl or 2,2,2-trifluoroethyl, $R^{24}$ is methyl or ethyl; and $R^{25}$ is methyl or ethyl.

Preferably, $R^1$ is —S(O)$_n$R$^7$, S(O)$_2$NHR$^8$,

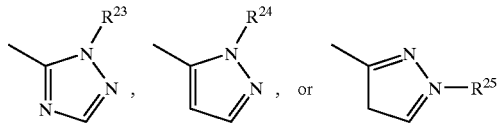

Most preferably, $R^1$ is —S(O)$_n$R$^7$.
Preferably, n is 2.
Preferably, $R^7$ is CH$_3$.
Preferably, $R^8$ is CH$_3$.
Preferably, $R^9$ is —NR$^{10}$R$^{11}$,

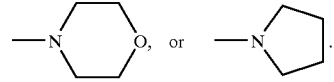

Preferably, $R^{11}$ is C$_{2-4}$alkyl or cylopropyl.
Preferably, at least one of $R^{18}$ and $R^{19}$ is —CH$_3$, —OCH$_3$, Cl, or F. Most preferably, $R^{21}$ and $R^{22}$ are H.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Suitable compounds of this invention include:
2-[(4,5-dihydro-1H-imidazol-2-ylmethyl)amino]-N-propylbenzamide
N-cyclopropyl-2-[(4,5-dihydro-1H-imidazol-2-ylmethyl)amino]benzamide
2-[(4,5-dihydro-1H-imidazol-2-ylmethyl)amino]-N-methylbenzamide
{2-[(4,5-dihydro-1H-imidazol-2-ylmethyl)amino]phenyl}(4-morpholinyl)methanone
2-[(4,5-dihydro-1H-imidazol-2-ylmethyl)amino]-N,N-diethylbenzamide
2-[(4,5-dihydro-1H-imidazol-2-ylmethyl)amino]-N-ethyl-N-methylbenzamide
2-[(4,5-dihydro-1H-imidazol-2-ylmethyl)amino]-N-methyl-N-propylbenzamide
N-(4,5-dihydro-1H-imidazol-2-ylmethyl)-2-(1,3-oxazol-5-yl)aniline
1-{2-[(4,5-dihydro-1H-imidazol-2-ylmethyl)amino]phenyl}-1-ethanone
N-(4,5-dihydro-1H-imidazol-2-ylmethyl)-2-(2-pyrazinyl)aniline
N-(4,5-dihydro-1H-imidazol-2-ylmethyl)-2-(2-methyl-1,3-thiazol-4-yl)aniline
N-(4,5-dihydro-1H-imidazol-2-ylmethyl)-2-(1-methyl-1H-pyrazol-3-yl)aniline
N-(4,5-dihydro-1H-imidazol-2-ylmethyl)-2-(1-methyl-1H-pyrazol-5-yl)aniline
N-(4,5-dihydro-1H-imidazol-2-ylmethyl)-2-(methylsulfonyl)aniline
2-[(4,5-dihydro-1H-imidazol-2-ylmethyl)amino]-N-methylbenzenesulfonamide
N-(4,5-dihydro-1H-imidazol-2-ylmethyl)-2-(1-methyl-1H-pyrrol-2-yl)aniline
N-(4,5-dihydro-1H-imidazol-2-ylmethyl)-2-(1-ethyl-1H-pyrazol-3-yl)aniline
N-(4,5-dihydro-1H-imidazol-2-ylmethyl)-2-(1-ethyl-1H-pyrazol-5-yl)aniline
2-[(4,5-dihydro-1H-imidazol-2-ylmethyl)amino]-N-ethylbenzenesulfonamide N-(4,5-dihydro-1H-imidazol-2-ylmethyl)-2-(1-ethyl-1H-pyrrol-2-yl)aniline
N-(4,5-dihydro-1H-imidazol-2-ylmethyl)-2-[1-(2,2,2-trifluoroethyl)-1H-1,2,4-triazol-5-yl]aniline
N-(4,5-dihydro-1H-imidazol-2-ylmethyl)-2-(ethylsulfonyl)aniline
N-(4,5-dihydro-1H-imidazol-2-ylmethyl)-5-fluoro-2-(methylsulfonyl)aniline
N-(4,5-dihydro-1H-imidazol-2-ylmethyl)-5-chloro-2-(methylsulfonyl)aniline
N-(4,5-dihydro-1H-imidazol-2-ylmethyl)-5-methyl-2-(methylsulfonyl)aniline
N-(4,5-dihydro-1H-imidazol-2-ylmethyl)-5-methoxy-2-(methylsulfonyl)aniline
N-(4,5-dihydro-1H-imidazol-2-ylmethyl)-2-[1-isopropyl-1H-1,2,4-triazol-5-yl]aniline
and pharmaceutically acceptable salts and solvates thereof.

Particularly preferred compounds of this invention include:
N-(4,5-dihydro-1H-imidazol-2-ylmethyl)-5-fluoro-2-(methylsulfonyl)aniline
N-(4,5-dihydro-1H-imidazol-2-ylmethyl)-2-(1-ethyl-1H-pyrazol-5-yl)aniline
2-[(4,5-dihydro-1H-imidazol-2-ylmethyl)amino]-N-methylbenzenesulfonamide
N-(4,5-dihydro-1H-imidazol-2-ylmethyl)-2-[1-(2,2,2-trifluoroethyl)-1H-1,2,4-triazol-5-yl]aniline
N-(4,5-dihydro-1H-imidazol-2-ylmethyl)-2-(methylsulfonyl)aniline
and pharmaceutically acceptable salts and solvates thereof.

The terms $C_{1-3}$alkyl, $C_{4-6}$cycloalkyl, $C_{3-6}$alkenyl and the like, as used herein, indicate groups that may contain the indicated range of carbon atoms, for example 1 to 3 carbon atoms. Unless otherwise indicated, such groups can be straight chained or branched.

Those skilled in the art will recognize that stereocenters exist in some compounds of Formula (I). Accordingly, the present invention includes all possible stereoisomers and geometric isomers of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (McGraw Hill, 1962) and *Tables of Resolving Agents* by S. H. Wilen. Additionally, in situations where tautomers of the compounds of formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of Formula (I) and their pharmaceutically acceptable salts and solvates.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of Formula (I) or a pharmaceutically acceptable salt or solvate thereof, preferably together with one or more pharmaceutically acceptable carriers therefor and, optionally, other therapeutic and/or prophylactic ingredients.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

The compounds in the invention can, in general, be prepared by reaction of an aniline with 2-(chloromethyl) imidazoline hydrochloride, as shown in Equation 1. This reaction generates the hydrochloride salt which may be isolated directly or if need be can be converted into the free base and then into other salt forms. The reaction is run in a protic solvent such as methanol, ethanol, methoxyethanol, isopropanol, butanol, or phenol, at temperatures from about 80–140° C. for about 10 minutes to 24 hours. Preferably the protic solvent is 2-butanol or isopropanol, most preferably 2-butanol. The preferred temperature for the reaction is 95–100° C. Preferably the reaction is carried out at a pH in the range pH 3.0–4.0. The product can be isolated by standard procedures known to one skilled in the art, such as extraction from aqueous at appropriate pH, crystallization, or chromatography on either silica or basic alumina. Similar procedures, as well as alternative routes can be found, for example in U.S. Pat. No. 4,414,223 (Copp et al.).

Equation 1

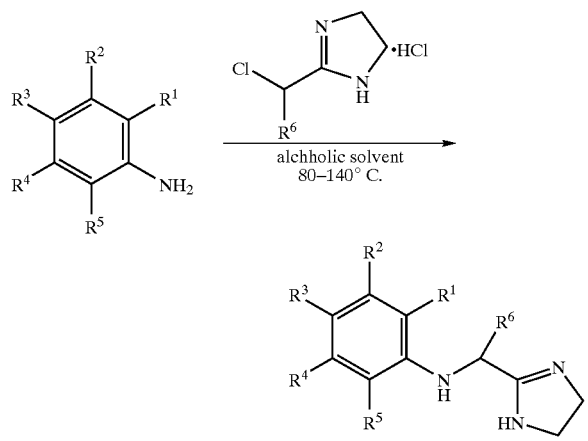

Many of the anilines can be obtained by reduction of an aromatic nitro group. Nitro reductions, for example as shown in Equation 2, can be performed by known methods. See, for example, M. Hudlicky, *Reductions in Organic Chemistry*, Second Edtition, ACS Mongraph 188, and European patent publication EP 0083975 B1 (Anthony Wolf et al.).

Equation 2

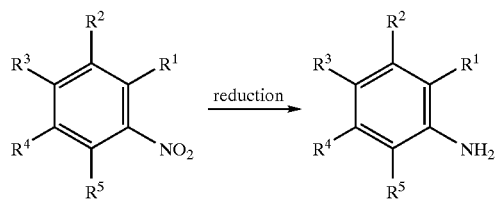

The reductions can, for example, be run by one or more of the following methods:

A) by catalytic hydrogenation with 5–10% palladium on charcoal, or platinum oxide, in an inert solvent such as ethanol at ambient temperature (see Hudlicky). Hydrogen may be introduced at atmospheric or at elevated pressure, 20–40 psi, for shorter reaction times, or via transfer from an appropriate source, such as hydrazine or ammonium formate. See, for example, Hudlicky, p. 15 and references therein.

B) with stannous chloride or tin and hydrochloric acid, either neat or in an inert solvent such as methanol, at about 25–80° C. for 0.5 to 10 hours. See, for example, G. Corsi, et al., *Boll. Chim. Farm.,* (1964), 103, 115; J. H. Finley, *J. Heterocycl. Chem.,* (1969), 6, 841; A. Quilico et al., *Gazz. Chim. Ital.,* (1946), 76, 87; and M. Khan and J. Poyla, *J. Chem. Soc. C.,* (1970), 85.

C) with sodium sulfide in 50% aqueous dioxane at about 25–80° C. for 0.25 to 1 hour or with sodium sulfide and sodium bicarbonate in refluxing methanol for 1 to 10 hours. For details refer to Y. Lin and S. Lang, Jr., *J. Heterocycl. Chem.,* (1980), 17, 1273 and P. Smith and J. Boyer, *J. Am. Chem. Soc.,* (1951), 73, 2626 respectively.

Many ortho-(imidazolidinyl, imidazolyl, oxazolyl, isoxazolyl, oxadiazolyl, thiazolyl, thiadiazolyl, triazolyl, or pyrazolyl) substituted nitro or aminophenyl intermediates can be prepared, for example as described in European patent EP 0083975 B1 (Anthony Wolf et al.).

Some ortho-pyrimidinyl substituted nitrophenyl intermediates can be prepared in an analogous fashion to the pyrazoles cited in European patent EP 0083975 B1, using amidines or guanidines in place of hydrazines.

Ortho-(pyrrolyl, pyrrolidinyl, piperidyl, azepinyl, and tetrazolyl) substituted nitrophenyl intermediates can be prepared by displacement of halogen from the corresponding ortho-halo nitrophenyl compound. For a review on aromatic nucleophilic substitution, see, for example, Zoltewicz, *Top. Curr. Chem.,* (1975), 59, 33–64.

Many ortho-(pyridyl, pyridazinyl, pyrimidinyl, pyrazinyl, furyl, thienyl, pyrrolyl and substituted phenyl) substituted amino or nitrophenyl intermediates can be prepared by a palladium mediated cross-coupling of either the ortho-halo nitrophenyl derivative and an appropriate boronic acid or trialkylstannane derivative, or the Boc-protected ortho-aminophenylboronic acid or trialkylstannane derivative and an appropriate halide partner. The protecting group can then be removed under standard conditions. See, for example, Green, *Protective Groups in Organic Synthesis,* Second Edition, Wiley and Sons, (1991). For procedures for the palladium catalyzed cross-coupling, see, for example, Snieckus et al., *J. Org. Chem.*, (1995), 60, 292 and Snieckus et al., *Synthesis*, (1989), 184. Many of these intermediates can also be prepared using an Ullman coupling. For a review, see, for example, Fanta, *Synthesis*, (1974), 9–21. Other commonly used methods for forming aryl-aryl bonds can be found, for example, in Bringmann et al., *Angew. Chem. Int. Ed. Engl.*, (1990), 29, 977–991.

Ortho-oxime ether substituted nitrophenyl derivatives can be prepared by condensation of an alkoxylamine with an ortho-nitrobenzaldehyde or phenylalkanone derivative under standard conditions. For details of a similar procedure, see, for example, Jencks, *J. Am. Chem. Soc.*, (1959), 81, 475 and *Prog. Phys. Org. Chem.*, (1964), 2, 63–128.

Anilines substituted at the ortho position with an amide can be prepared by opening isatoic anhydride with a primary or secondary amine, as demonstrated, for example, by R. Jacobs, *J. Heterocycl. Chem.*, (1970), 7, 1337–1345. Anilines substituted at the ortho position with hydrazides can be prepared in a similar manner, opening isatoic anhydride with substituted hydrazines, as described, for example, by F. Fulop and K. Pihlaja, *Org. Prep. Proced. Int.*, (1991), 23, 377–378.

This approach can be generalized to anilines with additional phenyl ring substituents, by opening substituted isatoic anhydrides. Substituted isatoic anhydrides can be prepared from the corresponding substituted 2-aminobenzoic acids by treatment with phosgene in toluene and aqueous sodium hydroxide solution, using a procedure described, for example, by G. Coppola and H. Schuster, *J. Heterocycl. Chem.*, (1989), 26, 957–964.

Anilines substituted with ketones at the ortho position can be prepared by several routes, including, for example, the addition of an alkylmagnesium halide to anthranilonitrile, followed by aqueous acid treatment. A relevant example of this well-known procedure, the synthesis of aminophenyl isopropyl ketone, can be found, for example, in J. Robl, *Synthesis*, (1991), 56–58.

Many substituted 2'-aminoacetophenones can be synthesized as described, for example, by R. Albrecht, *Liebigs Ann. Chem.*, (1978), 617–626. For example, 1-(2-aminophenyl)-2-(methylsulfonyl)ethanone, with or without additional phenyl ring substituents, can be prepared by treating the ester of the appropriate anthranilic acid with a solution of $MeSO_2CH_2Na$ in dimethylsulfoxide.

N-(4,5-dihydro-1H-imidazol-2-ylmethyl)-2-(alkylsulfonyl)anilines can be prepared, for example, by the general route from CMI and the appropriate 2-(alkylsulfonyl)anilines. Alternatively, N-(4,5-dihydro-1H-imidazol-2-ylmethyl)-2-(alkylsulfonyl)anilines, with or without additional phenyl ring substitutions, can be prepared, for example, by oxidation of the corresponding N-(4,5-dihydro-1H-imidazol-2-ylmethyl)-2-(alkylthio) anilines, for example, by using a variety of oxidants that are commonly employed to oxidize sulfides to sulfones, including, for example, m-chloroperoxybenzoic acid or potassium peroxymonosulfate (as OXONE®, Aldrich Chemical Co., Milwaukee, Wis.).

N-(4,5-dihydro-1H-imidazol-2-ylmethyl)-2-(alkylthio) anilines can be prepared, for example, by the general route from CMI and the appropriate 2-(alkylthio)aniline. Careful treatment with 1 equivalent of oxidant can be used to prepare N-(4,5-dihydro-1H-imidazol-2-ylmethyl)-2-(alkylsulfinyl) anilines from the corresponding N-(4,5-dihydro-1H-imidazol-2-ylmethyl)-2-(alkylthio)anilines. Enantiomers can be separated by preparative chiral column chromatography.

2-(alkylsulfonyl)anilines can be prepared by oxidation of the corresponding 2-(alkylthio)aniline using m-chloroperoxybenzoic acid. Alternatively, 2-(alkylsulfonyl)anilines can be prepared by reduction of the corresponding 2-(alkylsulfonyl)nitrobenzene. 2-(Alkylsulfonyl)nitrobenzenes can be prepared by several routes, including alkylation of a 2-nitrophenylsulfinate salt, derived from the corresponding 2-nitrophenylsulfonyl chloride. Several examples of phenylsulfinate salt alkylations are described by A. Goldberg and D. Besly, *J. Chem. Soc.*, 1945, 566–571.

2-(Alkylthio)anilines can be prepared by several routes, including alkylation of a 2-mercaptoaniline with an alkyl halide or other suitable alkyl electrophile. Thioether formation has been reviewed by Peach in Patai, *The Chemistry of the Thiol Group*, pt. 2; Wiley: New York, 721–735 (1974). Alternatively, 2-(alkylthio)anilines may be prepared by ortho-metallation of an appropriate trifluoroacetanilide, followed by quenching with an alkyl disulfide and removal of the trifluoroacetyl group with aqueous base, as described by B. McKittrick, et al., *J. Heterocycl. Chem.*, 1990, 27, 2151–2163. 2-(Alkylthio)anilines may also be prepared by addition of a mercaptan to an ortho-halonitrobenzene (ortho-fluoronitrobenzenenes are particularly suitable), as described by J. Slade, et al., *J. Med. Chem.*, 1985, 28, 1517–1521, followed by reduction of the nitro group using standard conditions.

Some 2-mercaptoanilines can be prepared by alkaline hydrolysis of an appropriate benzothiazole, as described by R. Gupta, et.al., *J. Heterocycl. Chem.*, 1980, 17, 1325–1327, and by T. Aotsuka, et al., *Chem. Pharm. Bull.*, 1994, 42, 1264–1271.

o-Amino-N-alkylbenzenesulfonamides can be prepared via the reaction of an alkylamine and an appropriate o-nitrobenzenesulfonyl chloride, followed by reduction of the nitro group using standard conditions. This common two-step approach is exemplified by A. Beckwith and G. Meiis, *J. Org. Chem.*, 1987, 52, 1922–1930, and by C. Mayfield and J. DeRuiter, *J. Med. Chem.*, 1987, 30, 1595–1598.

The following examples are set forth to illustrate the synthesis of some particular compounds of the present invention and to exemplify general processes. Accordingly, the following Examples section is in no way intended to limit the scope of the invention contemplated herein.

EXAMPLES 2-(Chloromethyl)-2-imidazoline Hydrochloride ("CMI")

This intermediate, prepared according to the method of Klarer and Urech; [*Helv. Chim. Acta*, 1944, 27, 1762–1773], was found to contain 18–25 mole % of $NH_4Cl$ by NMR. This material is used throughout the following experimentals; 2-(chloromethyl)-2-imidazoline hydrochloride will be commonly referred to as CMI.

This material could also be purified as follows. An 8.5 g sample of CMI, which was 18 mole % $NH_4Cl$ by NMR, was treated with 75 mL of ice cold 1N NaOH. This solution was saturated with NaCl and extracted with EtOAc, $CHCl_3$, and $Et_2O$. The combined extracts were dried and evaporated to give 5.75 g of a white solid. This free base was dissolved in 100 mL of $Et_2O$ and treated with 20 mL of 4N HCl in dioxane. A white precipitate formed. The slurry was stored in the freezer overnight. The CMI-HCl was filtered, washed with $Et_2O$, and dried under house vacuum in a desiccator, to yield 7.14 g of white solid, which was very pure by NMR.

General procedure for CMI coupling

The reaction is generally run in a protic solvent such as methanol, ethanol, methoxyethanol, isopropanol, butanol, or phenol, at temperatures from approximately 80–150° C. for 10 minutes to 24 hours, as needed. Typically, two equivalents of aniline are used, though less may be used if a base such as 2,6-lutidine is added. The product can be isolated by standard procedures known to one skilled in the art, such as extraction from aqueous at appropriate pH, crystallization, and/or chromatography on either silica or basic alumina. Often the products are converted to an appropriate acid addition salt, such as the hydrochloride or fumarate derivative. Similar procedures, as well as alternative routes can be found in U.S. Pat. No. 4,414,223.

Example 1

N-(4,5-Dihydro-1H-imidazol-2-ylmethyl)-2-(methylsulfonyl)aniline Fumarate

2-Methylmercaptoaniline (27.9 g, 200 mmol), CMI (13.5 g, 87 mmol), and phenol (10 g) were mixed in a round bottom flask under a nitrogen atmosphere and immersed in a 120° C. oil bath with magnetic stirring. After 70 minutes the reaction mixture was allowed to cool to ambient temperature and mixed thoroughly with ethyl acetate (100 mL) and water (500 mL). The organic phase was discarded and the aqueous phase was washed with four more volumes of ethyl acetate (100 mL each). Ethyl acetate (100 mL) was added and then 10N sodium hydroxide (9 mL) was added slowly to the stirred mixture. The ethyl acetate phase was discarded. 10N sodium hydroxide (13 mL) was added and the mixture was extracted four times with ethyl acetate (100 mL each). The combined extracts were dried ($MgSO_4$) and evaporated in vacuo to give N-(4,5-dihydro-1H-imidazol-2-ylmethyl)-2-(methylthio)aniline (16.8 g, 87%).

N-(4,5-Dihydro-1H-imidazol-2-ylmethyl)-2-(methylthio)aniline (16.8 g, 76 mmol) was stirred in methanol (250 mL) and cooled in an ice bath. A solution of m-chloroperoxybenzoic acid (37 g of ~70 wt %) in methanol (200 mL) was added dropwise over 1 hour while the temperature of the mixture was maintained below 28° C. After 20 minutes, additional m-chloroperoxybenzoic acid (2.0 g) was added and stirring continued for 20 minutes. The reaction mixture was reduced in vacuo to a slurry (~40 mL volume), diluted with water (250 mL) and ethyl acetate (250 mL), and treated with 10N sodium hydroxide (15 mL). The ethyl acetate phase and five additional ethyl acetate extracts (100 mL each) were combined and washed with 0.1N NaOH (50 mL). Additional 10N sodium hydroxide (10 mL) was added to the aqueous phase and two ethyl acetate extracts (100 mL each) were collected and washed with 0.1N NaOH (10 mL) and all of the ethyl acetate phases combined. Drying ($MgSO_4$) followed by evaporation gave N-(4,5-dihydro-1H-imidazol-2-ylmethyl)-2-(methylsulfonyl)aniline (12.3 g, 48.5 mmol), which was dissolved in ethyl acetate (450 mL). Fumaric acid (5.6 g, 48.5 mmol) was dissolved in methanol (80 mL) and the ethyl acetate solution of N-(4,5-dihydro-1H-imidazol-2-ylmethyl)-2-(methylsulfonyl)aniline was added to the rapidly stirred methanolic solution of fumaric acid. The mixture was stored at 4° C. for 16 hours and the resulting crystals were collected and dried in vacuo to give N-(4,5-dihydro-1H-imidazol-2-ylmethyl)-2-(methylsulfonyl)aniline as the fumaric acid salt (12.8 g, 45%).

$^1$H NMR (400 MHz, DMSO-$d_6$) δ 10.96 (brs); 7.65 (d, J=7.8 Hz, 1H); 7.49 (dd, $J_{AB}$=7.5 Hz, $J_{AC}$=7.5 Hz, 1H); 6.85 (dd, $J_{AB}$=7.5 Hz, 1H); 6.78 (d, J=8.3 Hz, 1H); 6.73 (t, J=5.8 Hz, 1H); 6.46 (s, 2H); 4.36 (d, J=5.5 Hz, 2H); 3.73 (s, 4H); 3.19 (s, 3H). $^{13}$C NMR 168.5, 167.7, 145.5, 135.4, 135.1, 129.5, 122.2, 116.9, 112.4, 45.6, 42.6, 42.6. Mass. Spec. 254 (100%) (M+H); 184 (85%) (M+H−70). Anal. Calc'd for $C_{15}H_{19}N_3SO_6$: C 48.77, H 5.18, N 11.38, S 8.68 Found: C 48.86, H 5.17, N 11.27, S 8.73. IR (KBr) (cm$^{-1}$) 3348, 3088, 2933, 2786, 2670, 1698, 1598, 1518, 1462, 1368, 1285, 1132, 1047, 754, 646, 520.

Example 2

N-(4,5-Dihydro-1H-imidazol-2-ylmethyl)-2-(ethylsulfonyl)aniline Fumarate

2-Aminothiophenol (5.0 g, 40 mmol, Lancaster Synthesis Inc., Windham, N.H.) was stirred in dry ethanol (100 mL) and cooled in an ice bath. Potassium t-butoxide (4.5 g, 40 mmol) was added portionwise over 15 minutes and the mixture was stirred for an additional 45 minutes. Ethyl iodide (3.3 mL, 41 mmol) was added dropwise over 15 minutes and the mixture was allowed to warm to room temperature and stirred for 45 minutes. The mixture was filtered and the filtrate evaporated to dryness in vacuo. The resulting residue was treated with dichloromethane (100 mL) and filtered and the resulting filtrate was evaporated to dryness in vacuo to give 2-(ethylthio)aniline (5.2 g).

N-(4,5-Dihydro-1H-imidazol-2-ylmethyl)-2-(ethylthio)aniline was prepared from 2-(ethylthio)aniline and CMI, oxidized, and the resulting sulfone isolated using the general methods described in Example 1 to provide N-(4,5-dihydro-1H-imidazol-2-ylmethyl)-2-(ethylsulfonyl)aniline as the fumarate salt.

$^1$H NMR (400 MHz, DMSO-$d_6$) δ 10.95 (brs); 7.60 (d, J=7.5 Hz, 1H); 7.50 (dd, $J_{AB}$=7.5 Hz, $J_{AC}$=7.5 Hz, 1H); 6.85 (dd, $J_{AB}$=7.5 Hz, $J_{AC}$=7.5 Hz, 1H); 6.78 (d, J=8.3 Hz, 1H); 6.73 (t, J=5.8 Hz, 1H); 6.46 (s, 2H); 4.23 (d, J=5.5 Hz, 2H); 3.70 (s, 4H); 3.28 (q, J=7.3 Hz, 2H); 1.08 (t, J=7.3 Hz, 3H). Mass. Spec. 268 (50%) (M+H); 198 (100%) (M+H−70).

Example 3

N-(4,5-Dihydro-1H-imidazol-2-ylmethyl)-2-(isopropylsulfonyl)aniline Fumarate

N-(4,5-Dihydro-1H-imidazol-2-ylmethyl)-2-(isopropylsulfonyl)aniline was prepared and isolated as the fumarate salt using the general methods described in Example 1. The 2-(Isopropylthio)aniline used in the synthesis was prepared from 2-aminothiophenol and isopropyl iodide using the method described in Example 2.

Example 4

N-(4,5-Dihydro-1H-imidazol-2-ylmethyl)-2-fluoro-6-(methylsulfonyl)aniline Fumarate 2,6-Difluoronitrobenzene (1.0 g, 6.3 mmol) was stirred in ethanol (10 mL) and treated with sodium methylmercaptan (0.44 g, 6.3 mmol) in several portions over 5 minutes. After stirring for 2 hours the mixture was evaporated and chromatographed on silica gel (70% hexane:30% ethyl acetate) to give 2-methylmercapto-6-fluoronitrobenzene (approximately 1.0 g), which was reduced in ethanol (30 mL) using 5% palladium on carbon (0.3 g) and hydrogen (50 psi) for 2 hours. The catalyst was removed by filtration through celite and the solvent evaporated to give 2-fluoro-6-(methylthio)benzenamine (0.69 g).

N-(4,5-Dihydro-1H-imidazol-2-ylmethyl)-2-fluoro-6-(methylsulfonyl)aniline was prepared from 2-fluoro-6-(methylthio)benzenamine using the two-step procedure described in Example 1, and isolated as the fumarate salt.

Example 5

N-(4,5-Dihydro-1H-imidazol-2-ylmethyl)-4-fluoro-2-(methylsulfonyl)aniline Fumarate 2-Amino-6-fluorobenzothiazole (5.0 g, 29.7 mmol) was stirred in 10N NaOH (120 mL) and heated to 120° C. After 2 hours the mixture was allowed to cool and treated with acetic acid (~70 mL) to adjust the pH of the mixture to 4.0. The resulting precipitate was collected and washed with 3 volumes (30 mL) of water and dried in vacuo to give 5.5 g of 2-amino-5-fluorothiophenol suitable for use in the subsequent step.

Under conditions similar to those used for the preparation of 2-(ethylthio)aniline in Example 2, 2-amino-5-fluorothiophenol was alkylated with methyl iodide to give 2-methylthio-4-fluoroaniline.

N-(4,5-Dihydro-1H-imidazol-2-ylmethyl)-4-fluoro-2-(propylmercapto)aniline was prepared from 2-methylthio-4-fluoroaniline using the two-step procedure described in Example 1, and isolated as the fumarate salt.

Example 6

N-(4,5-Dihydro-1H-imidazol-2-ylmethyl)-2-(propylsulfonyl)aniline Hydrochloride

Sodium hydrogensulfite (50 g, 480 mmol) and sodium bicarbonate (35 g, 416 mmol) were heated to 80° C. in water (200 mL). 2-Nitrobenzenesulfonyl chloride (47 g, 212 mmol) was added in several portions over 90 minutes and the mixture was stirred for two hours at 80° C., then allowed to cool to ambient temperature. The resulting solid was collected, washed with ice water and dried in vacuo to give the intermediate sulfinic acid (crude yield 28.6 g). The sulfinic acid (9.5 g) was treated with sodium bicarbonate (11 g), water (5 mL) and 1-bromopropane (9.8 mL). The mixture was stirred, and an additional 15 mL water was added over 1 hour. The mixture was heated to 90° C. under nitrogen and stirred for 16 hours. After cooling, the mixture was extracted with toluene (3×100 mL) and the extracts evaporated to give crude 1-nitro-2-(propylsulfonyl)benzene (0.6 g). Silica gel chromatography (7:1 hexane:$CH_2Cl_2$) gave product (0.34 g).

Reduction of 1-nitro-2-(propylsulfonyl)benzene (0.34 g, 1.7 mmol) with hydrogen (50 psi) and 5% Pd on carbon (0.1 g) in ethanol (50 mL) for 1 hour gave 2-(propylsulfonyl)benzenamine (0.29 g) after filtration and evaporation.

2-(Propylsulfonyl)benzenamine was reacted with CMI using the general methods for CMI coupling to give N-(4,5-dihydro-1H-imidazol-2-ylmethyl)-2-(propylsulfonyl)aniline. 1 equivalent of 4N HCl in dioxane was used to form the hydrochloride salt.

Example 7

N-(4,5-Dihydro-1H-imidazol-2-ylmethyl)-3fluoro-2-(methylsulfonyl)aniline Fumarate N-(2-Methylthio-3-fluorophenyl)trifluoroacetamide (2.36 g crude, 9.33 mmol, prepared as described by McKittrick, *J. Het. Chem.* 1990, 27, 2151–2163) was taken up in methanol (40 mL), and solid potassium hydroxide (1.57 g, 28.0 mmol) was added portionwise at room temperature. The mixture was heated to reflux. After 1.5 hours, the mixture was cooled to room temperature, and the solvent volume reduced to 5 mL by evaporation under reduced pressure. The residue was taken up in deionized water (30 mL) and extracted with diethyl ether (3×40 mL). The extracts were combined, washed with saturated sodium chloride solution, dried over sodium sulfate, and the volatiles were removed by evaporation under reduced pressure. The product was purified by silica gel chromatography using 10% ethyl acetate in hexanes. 1.2 g of 3-fluoro-2-(methylthio)aniline was isolated.

N-(4,5-Dihydro-1H-2-ylmethyl)-3-fluoro-2-(methylsulfonyl)aniline was prepared from 3-fluoro-2-(methylthio)aniline using the two-step procedure described in Example 1, and isolated as the fumarate salt.

Example 8

N-(4,5-Dihydro-1H-imidazol-2-ylmethyl)-5-fluoro-2-(methylsulfonyl)aniline Fumarate 5-Fluoro-2-methylbenzothiazole was heated with ethylene glycol and 10N sodium hydroxide solution and the resulting thiol methylated using procedures similar to those described in Example 5, to give 5-fluoro-2-(methylthio) aniline.

N-(4,5-Dihydro-1H-imidazol-2-ylmethyl)-5-fluoro-2-(methylsulfonyl)aniline was prepared from 5-fluoro-2-(methylthio)aniline using the two-step procedure described in Example 1, and isolated as the fumarate salt.

$^1$H NMR (400 MHz, DMSO-$d_6$) δ 7.70 (dd, $J_1$=6.6 Hz, $J_2$=8.8 Hz, 1H); 6.91 (br s, 1H); 6.63–6.68 (m, 2H); 6.48 (s, 2H); 4.23 (d, J=5.3 Hz, 2H); 3.67 (s, 4H); 3.19 (s, 3). Mass. Spec. 272 (100%) (M+H); 193 (90%).

Example 9

N-(4,5-Dihydro-1H-imidazol-2-ylmethyl)-5-methoxy-2-(methylsulfonyl)aniline Fumarate Starting from 5-methoxy-2-methylbenzothiazole, N-(4,5-dihydro-1H-imidazol-2-ylmethyl)-5-methoxy-2-(methylsulfonyl)aniline fumarate was prepared and isolated using the procedures described in Example 8.

$^1$H NMR (300 MHz; DMSO-$d_6$): δ 3.15 (s, 3H), 3.70 (s, 4H), 3.82 (s, 3H), 4.25 (d, J=5.2 Hz, 2H), 6.23 (br d, J=2.0 Hz, 1H), 6.45 (br dd, J=8.9 Hz, 2.1 Hz, 1H), 6.49 (s, 2H), 6.74 (br t, J=5.3 Hz, 1H), 7.59 (d, J=8.9 Hz, 1H). Mass. Spec. 284 (90%) (M+H).

Example 10

N-(4,5-Dihydro-1H-imidazol-2-ylmethyl)-5-methyl-2-(methylsulfonyl)aniline Fumarate Starting from 2,5-dimethylbenzothiazole, N-(4,5-dihydro-1H-imidazol-2-ylmethyl)-5-methyl-2-(methylsulfonyl)aniline fumarate was prepared and isolated using the procedures described in Example 8.

$^1$H NMR (400 MHz, DMSO-$d_6$): δ 7.53 (d, J=8.0 Hz, 1H), 6.62–6.68 (m, 3H); 6.47 (s, 2H); 4.26 (br s, 2H); 3.71 (s, 4H); 3.17 (s, 3H); 2.30 (s, 3H). Mass. Spec. 268 (100%) (M+H).

Example 11

N-(4,5-Dihydro-1H-imidazol-2-ylmethyl)-2-(methylsulfinyl)aniline Hydrochloride Salt N-(4,5-Dihydro-1H-imidazol-2-ylmethyl)-2-(methylthio) aniline (32 mg, 0.144 mmol, prepared as described in Example 1) was stirred in dichloromethane (1 mL) and treated with m-chloroperoxybenzoic acid (35 mg of 70 wt %). After 15 minutes the mixture was evaporated and treated with ether (2 mL), 3 drops of methanol, and then 1N HCl in ether (0.2 mL). The resulting precipitate was collected and washed with ether (1 mL) to give N-(4,5-dihydro-1H-imidazol-2-ylmethyl)-2-(methylsulfinyl)aniline hydrochloride salt (30 mg).

Example 12

(−)-N-(4,5-Dihydro-1H-imidazol-2-ylmethyl)-2-(methylsulfinyl)aniline Fumaric Acid Salt A sample of the enantiomeric mixture of N-(4,5-dihydro-1H-imidazol-2-ylmethyl)-2-(methylsulfinyl)aniline hydrochloride salt, prepared in Example 11, was converted to the free base and chromatographed on a Daicel OD column (21.5×250 mm) using an eluent mixture of ethanol (8% v/v) in hexane with diisopropylethylamine (0.2% v/v) at 8 ml/min flow rate. The earlier eluting enantiomer (22.5 min) was converted to its fumaric acid salt and determined to be (−)-N-(4,5-dihydro-1H-imidazol-2-ylmethyl)-2-(methylsulfinyl)aniline by measurement of its optical rotation in methanol.

Example 13

(+)-N-(4,5-dihydro-1H-imidazol-2-ylmethyl)-2-(methylsulfinyl)aniline Fumaric Acid Salt The later eluting enantiomer from Example 12 (24 min) was converted to its fumaric acid salt and determined to be (+)-N-(4,5-dihydro-1H-imidazol-2-ylmethyl)-2-(methylsulfinyl)aniline by measurement of its optical rotation in methanol.

Example 14

1-{2-[(4,5-Dihydro-1H-imidazol-2-ylmethyl)amino]phenyl}-2-(methylsulfonyl)-1-ethanone Dimethylsulfone (120 g, 1.28 mol) was stirred in DMSO (350 mL). Sodium hydride (48 g of 60 wt % in mineral oil) was added in portions and the mixture heated to 60° C. Methyl anthranilate (48.3 g, 0.32 mol) was added dropwise over 3 hours while the temperature rose to 100° C. The mixture was poured into ice (500 mL) and concentrated HCl (100 mL) and the mixture stored at 4° C. overnight. The mixture was extracted with dichloromethane (3×400 mL), and the combined extracts were washed with saturated bicarbonate (3×30 mL), dried ($MgSO_4$), and reduced to 800 mL volume. The solid that formed was removed by filtration. The filtrate was reduced to 80 mL volume. The resulting solid was collected and washed with a small volume of dichloromethane. The solid was recrystallized from chloroform to give 1-(2-aminophenyl)-2-(methylsulfonyl) ethanone (24 g).

1-{2-[(4,5-Dihydro-1H-imidazol-2-ylmethyl)amino]phenyl}-2-(methylsulfonyl)-1-ethanone was prepared from 1-(2-aminophenyl)-2-(methylsulfonyl)ethanone and CMI using the general procedure for CMI coupling.

Example 15

N-(tert-Butyl)-2-[(4,5-dihydro-1H-imidazol-2ylmethyl)amino]benzamide

2-Amino-N-tert-butylbenzamide (Trans World Chemicals) was reacted with CMI using the general procedure for CMI coupling to give N-(tert-butyl)-2-[(4,5-dihydro-1H-imidazol-2-ylmethyl)amino]benzamide.

Example 16

2-[(4,5-Dihydro-1H-imidazol-2-ylmethyl)amino]-N-methylbenzamide Hydrochloride

2-Amino-N-methylbenzamide was reacted with CMI using conditions described in the general procedure for CMI coupling to give 2-[(4,5-dihydro-1H-imidazol-2-ylmethyl)amino]-N-methylbenzamide hydrochloride.

$^1$H NMR (300 MHz; DMSO-$d_6$): δ 2.74 (d, J=4.3 Hz, 3H), 3.80 (s, 4H), 4.34 (d, J=6.0 Hz, 2H), 6.53 (d, J=8.3 Hz, 1H), 6.69 (dd, J=7.5 Hz, 7.5 Hz, 1H), 7.30 (dd, J=7.7 Hz, 7.7 Hz, 1H), 7.57 (d, J=7.6 Hz, 1H), 8.22 (br t, J=6.1 Hz, 1H), 8.40 (m, 1H), 10.07 (br s, 2H). Mass. Spec. 233 (95%) (M+H).

Example 17

{2-[(4,5-Dihydro-1H-imidazol-2-ylmethyl)amino]phenyl}(1-pyrrolidinyl)methanone Fumarate Pyrrolidine (2.46 g, 34.6 mmol) was added dropwise to isatoic anhydride (3.76 g, 23.05 mmol) in tetrahydrofuran (25 mL) at room temperature. The solution was stirred at room temperature for 1.5 hours under a nitrogen atmosphere. The volatiles were removed by evaporation under reduced pressure. The residue was slurried in toluene (50 mL) and the volatiles were removed by evaporation under reduced pressure (2×). The residue was dissolved in hot toluene, then allowed to cool to room temperature. The solution was placed in a freezer for 16 hours to produce a precipitate. The precipitate was filtered and dried to give 3.05 g of crude 1-(2-aminobenzoyl)-pyrrolidine. The crude material (2.65 g) was purified by column chromatography over silica gel using 5–20% ethyl acetate in hexanes. The best fractions were combined and the volatiles were removed by evaporation under reduced pressure. The residue was taken up in dichloromethane (50 mL) and washed with 0.5N sodium hydroxide solution (2×25 mL), washed with saturated sodium chloride solution, dried over sodium sulfate, filtered and the filtrate was concentrated under reduced pressure to yield 1.35 g of 1-(2-aminobenzoyl) pyrrolidine.

The fumarate salt of {2-[(4,5-dihydro-1H-imidazol-2-ylmethyl)amino]phenyl}(1-pyrrolidinyl)methanone was prepared from 1-(2-aminobenzoyl)pyrrolidine and CMI using the general procedure for CMI coupling.

Example 18

N-Butyl-2-[(4,5-dihydro-1H-imidazol-2-ylmethyl)amino]benzamide Hydrochloride

2-Amino-N-butylbenzamide (prepared from butylamine and isatoic anhydride, using the methods described in Example 17) and CMI were reacted using conditions described in the general procedure for CMI coupling to give N-butyl-2-[(4,5-dihydro-1H-imidazol-2-ylmethyl)amino] benzamide, isolated as the hydrochloride salt.

Example 19

2-[(4,5-Dihydro-1H-imidazol-2-ylmethyl)amino]-N-isopropyl-N-methylbenzamide

2-Amino-N-isopropyl-N-methylbenzamide (prepared from N-methylisopropylamine and isatoic anhydride, using the methods described in Example 17) and CMI were reacted using conditions described in the general procedure for CMI coupling to give 2-[(4,5-dihydro-1H-imidazol-2-ylmethyl)amino]-N-isopropyl-N-methylbenzamide.

Example 20

2-[(4,5-Dihydro-1H-imidazol-2-ylmethyl)amino]-N-methyl-N-propylbenzamide

2-Amino-N-methyl-N-propylbenzamide (prepared from N-methylpropylamine and isatoic anhydride, using the methods described in Example 17) and CMI were reacted using conditions described in the general procedure for CMI coupling to give 2-[(4,5-dihydro-1H-imidazol-2-ylmethyl)amino]-N-methyl-N-propylbenzamide.

¹H NMR (300 MHz; DMSO-d₆): δ 0.77 (br s, 3H), 1.50 (br s, 2H), 2.87 (br s, 3H), 3.24 (br s, 2H) (Resonance observed upon addition of D₂O), 3.42 (s, 4H), 3.73 (d, J=4.6 Hz, 2H), 5.53 (m, 1H), 6.61 (m, 3H), 7.00 (d, J=7.2 Hz, 1H), 7.18 (dd, J=7.6 Hz, 7.6 Hz, 1H). Mass. Spec. 275 (25%) (M+H).

Example 21

2[(4,5-Dihydro-1H-imidazol-2-ylmethyl)amino]-N-propylbenzamide Hydrochloride

2-Amino-N-propylbenzamide (prepared from propylamine and isatoic anhydride, using, the methods described in Example 17) and CMI were reacted using conditions described in the general procedure for CMI coupling to give 2-[(4,5-dihydro-1H-imidazol-2-ylmethyl)amino]-N-propylbenzamide, isolated as the hydrochloride salt.

¹H NMR (300 MHz; DMSO-d₆): δ 0.88 (t, J=7.4 Hz, 3H), 1.52 (m, 2H), 3.17 (m, 2H), 3.80 (s, 4H), 4.34 (d, J=6.0 Hz, 2H), 6.53 (d, J=8.3 Hz, 1H), 6.70 (dd, J=7.5 Hz, 7,5 Hz, 1H), 7.30 (dd, J=7.7 Hz, 7.7 Hz, 1H), 7.61 (d, J=7.5 Hz, 1H), 8.23 (br t,. J=6.0 Hz, 1H), 8.43 (br t, J=5.3 Hz, 1H), 10.07 (br s, 2H). Mass. Spec. 261(90%) (M+H).

Example 22

N-Allyl-2-[(4,5-dihydro-1H-imidazol-2-ylmethyl)amino]benzamide hydrochloride

N-Allyl-2-amino benzamide (prepared from allylamine and isatoic anhydride, using the methods described in Example 17) and CMI were reacted using conditions described in the general procedure for CMI coupling to give N-allyl-2-[(4,5-dihydro-1H-imidazol-2-ylmethyl)amino]benzamide, isolated as the hydrochloride salt.

Example 23

{2-[(4,5-Dihydro-1H-imidazol-2-ylmethyl)amino]phenyl}(1-piperidinyl)methanone 1-(2-Aminobenzoyl)piperidine (prepared from piperidine and isatoic anhydride, using the methods described in Example 17) and CMI were reacted using conditions described in the general procedure for CMI coupling to give {2-[(4,5-dihydro-1H-imidazol-2-ylmethyl)amino]phenyl}(1-piperidinyl)methanone.

Example 24

2-[(4,5-Dihydro-1H-imidazol-2-ylmethyl)amino]-N-(1-ethylpropyl)benzamide

2-Amino-N-(1-ethylpropyl)benzamide (prepared from 1-ethylpropylamine and isatoic anhydride, using the methods described in Example 17) and CMI were reacted using conditions described in the general procedure for CMI coupling to give 2-[(4,5-dihydro(1H-imidazol-2-ylmethyl)amino]-N-(1-ethylpropyl)benzamide.

Example 25

2-[(4,5-Dihydro-1H-imidazol-2-ylmethyl)amino]-N-(2-methoxyethyl)-N-methylbenzamide 2-Amino-N-(2-methoxyethyl)-N-methylbenzamide (prepared from N-(2-methoxyethyl)methylamine and isatoic anhydride, using the methods described in Example 17) and CMI were reacted using conditions described in the general procedure for CMI coupling to give 2-[(4,5-dihydro-1H-imidazol-2-ylmethyl)amino]-N-(2-methoxyethyl)-N-methylbenzamide.

Example 26

2-[(4,5-Dihydro-1H-imidazo-2-ylmethyl)amino]-N-isopropylbenzamide

2-Amino-N-isopropylbenzamide (prepared from isopropylamine and isatoic anhydride, using the methods described in Example 17) and CMI were reacted using conditions described in the general procedure for CMI coupling to give 2-[(4,5-dihydro-1H-imidazol-2-ylmethyl)amino]-N-isopropylbenzamide.

Example 27

2-[(4,5-Dihydro-1H-imidazol-2-ylmethyl)amino]-N-(2-hydroxypropyl)benzamide hydrochloride 2-Amino-N-(2-hydroxypropyl)benzamide (prepared from 1-amino-2-propanol and isatoic anhydride, using the methods described in Example 17) and CMI were reacted using conditions described in the general procedure for CMI coupling to give 2-[(4,5-dihydro-1H-imidazol-2-ylmethyl)amino)-N-(2-hydroxypropyl)benzamide, isolated as the hydrochloride salt.

Example 28

N-Cylopropyl-2-[(4,5-dihydro-1H-imidazol-2-ylmethyl)amino]benzamide hydrochloride 2-Amino-N-cyclopropylbenzamide (prepared from cyclopropylamine and isatoic anhydride, using the methods described in Example 17) and CMI were reacted using conditions described in the general procedure for CMI coupling to give N-cyclopropyl-2-[(4,5-dihydro-1H-imidazol-2-ylmethyl)amino]benzamide, isolated as the hydrochloride salt.

¹H NMR (300 MHz; DMSO-d₆): δ 0.56 (m, 2H), 0.67 (m, 2H), 2.81(m,1H), 3.80 (s, 4H), 4:34 (d, J=6.0 Hz, 2H), 6.52 (d, J=8.3 Hz, 1H), 6.67 (dd, J=7.5 Hz, 7.5 Hz, 1H), 7.29 (dd, J=7.6 Hz, 7.6 Hz, 1H), 7.55 (d, J=7.5 Hz, 1H), 8.22 (br t, J=6.0 Hz, 1H), 8.38 (br d, J=3.8 Hz, 1H), 10.05 (br s, 2H). Mass. Spec. 259 (95%) (M+H).

Example 29

2-[(4,5-Dihydro-1H-imidazol-2-ylmethyl)amino]-N,N-dimethylbenzamide

2-Amino-N,N-dimethylbenzamide (prepared from dimethylamine [2M in tetrahydrofuran]and isatoic anhydride, using the methods described in Example 17) and CMI were reacted using conditions described in the general procedure for CMI coupling to give 2-[(4,5-dihydro-1H-imidazol-2-ylmethyl)amino]-N,N-dimethylbenzamide.

Example 30

{2-[(4,5-Dihydro-1H-imidazol-2-ylmethyl)amino]phenyl}(4-morpholinyl)methanone 1-(2-Aminobenzoyl)morpholine (prepared from morpholine and isatoic anhydride, using the methods described in Example 17) and CMI were reacted using conditions described in the general procedure for CMI coupling to give {2-[(4,5-dihydro-1H-imidazol-2-ylmethyl)amino]phenyl)(4-morpholinyl)methanone.

¹H NMR (300 MHz; DMSO-d₆): δ 3.43 (br s, 8H), 3.59 (m, 4H), 3.75 (d, J=4.7 Hz, 2H), 5.69 (br t, J=4.7 Hz, 1H), 6.62 (m, 2H), 7.05 (d, J=7.4 Hz, 1H), 7.21 (dd, J=7.6 Hz, 7.6 Hz, 1H). Mass. Spec. 289 (70%) (M+H).

Example 31

2-[(4,5-Dihydro-1H-imidazol-2-ylmethyl)amino]-N-pentylbenzamide

2-Amino-N-pentylbenzamide (prepared from amylamine and isatoic anhydride, using the methods described in Example 17) and CMI were reacted using conditions described in the general procedure for CMI coupling to give 2-[(4,5-dihydro-1H-imidazol-2-ylmethyl)amino]-N-pentylbenzamide.

Example 32

2-[(4,5-Dihydro-1H-imidazol-2-ylmethyl)amino]-N-ethylbenzamide

2-Amino-N-ethylbenzamide (prepared from ethylamine [2M in tetrahydrofuran] and isatoic anhydride, using the methods described in Example 17) and CMI were reacted using conditions described in the general procedure for CMI coupling to give 2-[(4,5-dihydro(1H-imidazol-2-ylmethyl)amino]-N-ethylbenzamide.

Example 33

2-[(4,5-Dihydro-1H-imidazol-2-ylmethyl)amino]-N-ethyl-N-propylbenzamide

2-Amino-N-ethyl-N-propylbenzamide (prepared from N-ethylpropylamine and isatoic anhydride, using the methods described in Example 17) and CMI were reacted using conditions described in the general procedure for CMI coupling to give 2-[(4,5-Dihydro-1H-imidazol-2-ylmethyl)amino]-N-ethyl-N-propylbenzamide.

Example 34

2-[(4,5-Dihydro-1H-imidazol-2-ylmethyl)amino]-N,N-diethylbenzamide fumarate

2-Amino-N,N-diethylbenzamide (prepared from diethylamine and isatoic anhydride, using the methods described in Example 17) and CMI were reacted using conditions described in the general procedure for CMI coupling to give 2-[(4,5-dihydro-1H-imidazol-2-ylmethyl)amino]-N,N-diethylbenzamide, isolated as the fumarate salt.

¹H NMR (400 MHz; DMSO-d₆): δ 1.08 (br s, 6H), 3.30 (br s, 4H), 3.70 (s, 4H), 4.13 (d, J=5.6 Hz, 2H), 5.66 (br t, J=5.7 Hz, 1H), 6.44 (s, 2H), 6.64 (d, J=8.2 HZ, 1H), 6.71(dd, J=7.4 Hz, 7.4 Hz, 1H), 7.03 (d, J=6.7 Hz, 1H), 7.21 (dd, J=7.7 Hz, 7.7 Hz, 1H). Mass. Spec. 275 (40%) (M+H).

Example 35

N-(Cyclopropylmethyl)-2-[(4.5-dihydro(1H-imidazol-2-ylmethyl)amino]-N-propylbenzamide 2-Amino-N-(cyclopropylmethyl)-N-propylbenzamide (prepared from N-propylcyclopropanemethylamine and isatoic anhydride, using the methods described in Example 17) and CMI were reacted using conditions described in the general procedure for CMI coupling to give N-(cyclopropylmethyl)-2-[(4,5-dihydro-1H-imidazol-2-ylmethyl)amino]-N-propylbenzamide.

Example 36

2-[(4.5-Dihydro-1H-imidazol-2-ylmethyl)amino]-N-ethyl-N-methylbenzamide

2-Amino-N-ethyl-N-methylbenzamide (prepared from N-ethylmethylamine and isatoic anhydride, using the methods described in Example 17) and CMI were reacted using conditions described in the general procedure for CMI coupling to give 2-[(4,5-dihydro-1H-imidazol-2-ylmethyl)amino]-N-ethyl-N-methylbenzamide.

1H NMR (300 MHz; DMSO-d₆): δ 1.07 (m, 3H), 2.88 (br s, 3H), 3.32 (br s, 2H) (Resonance believed to be coincident with water peak based on precedent established for 2-[(4,5-dihydro-1H-imidazol-2-ylmethyl)amino]-N-methyl-N-propylbenzamide), 3.43 (s, 4H), 3.74 (d, J=4.9 Hz, 2H), 5.54 (m, 1H), 6.61 (m, 3H), 7.01 (d, J=7.0 Hz, 1H), 7.19 (dd, J=7.6 Hz, 7.6 Hz, 1H). Mass. Spec. 261(8%) (M+H).

Example 37

N-(sec-Butyl)-2-[(4,5-dihydro-1H-imidazol-2-ylmethyl)amino]benzamide

2-Amino-N-sec-butylbenzamide (prepared from sec-butylamine and isatoic anhydride, using the methods described in Example 17) and CMI were reacted using conditions described in the general procedure for CMI coupling to give N-(sec-butyl-2-[(4,5-dihydro-1H-imidazol-2-ylmethyl)amino]benzamide.

Example 38

N-Butyl-2-[(4,5-dihydro-1H-imidazol-2-ylmethyl)amino]-5-fluorobenzamide hydrochloride 2-Amino-5-fluorobenzoic acid (1.91 g, 12.3 mmol) was dissolved in 1N sodium hydroxide solution (15 mL) and cooled to 0° C. under a nitrogen atmosphere. Phosgene (10 mL of a 20% solution in toluene) was added dropwise. After the addition was complete, the thick slurry was allowed to warm to room temperature. The precipitate was filtered off and rinsed with deionized water (2×50 mL). The precipitate was slurried in diethyl ether (50 mL), filtered, and dried under reduced pressure to yield 2.04 g of 6-fluoro-2H-3,1-benzoxazine-2,4(1H)-dione.

2-Amino-N-butyl-5-fluorobenzamide (prepared from butylamine and 6-fluoro-2H-3,1-benzoxazine-2,4(1H)-dione using the methods described in Example 17) and CMI were reacted using conditions described in the general procedure for CMI coupling to give N-butyl-2-[(4,5-dihydro-1H-imidazol-2-ylmethyl)amino]-5-fluorobenzamide, isolated as the hydrochloride salt.

Example 39

N-Cyclopropyl-2-[(4,5-dihydro-1H-imidazol-2-ylmethyl)amino]-5-fluorobenzamide

2-Amino-N-cyclopropyl-5-fluorobenzamide (prepared from cyclopropylamine and 6-fluoro-2H-3,1-benzoxazine-2,4(1H)-dione using the methods described in Example 17) and CMI were reacted using conditions described in the general procedure for CMI coupling to give N-cyclopropyl-2-[(4,5-dihydro-1H-imidazol-2-ylmethyl)amino]-5-fluorobenzamide.

Example 40

N-Cyclopropyl-2-[(4,5-dihydro-1H-imidazol-2-ylmethyl)amino]-6-methylbenzamide

5-Methyl-2H-3,1-benzoxazine-2,4(1H)-dione was prepared from 2-amino-6-methylbenzoic acid using the method described in Example 38.

2-Amino-N-cyclopropyl-6-methylbenzamide (prepared from cyclopropylamine and 5-methyl-2H-3,1-benzoxazine-2,4(1H)-dione using the methods described in Example 17) and CMI were reacted using conditions described in the general procedure for CMI coupling to give N-cyclopropyl-2-[(4,5-dihydro-1H-imidazol-2-ylmethyl)amino]-6-methylbenzamide.

Example 41

{2-[(4,5-Dihydro-1H-imidazol-2-ylmethyl)amino]-6-fluoroohenyl}(1-pyrrolidioyl)methanone 5-Fluoro-2H-3,1-benzoxazine-2,4(1H)-dione was prepared from 2-amino-6-fluorobenzoic acid using the method described in Example 38.

{2-Amino-6-fluorophenyl}(1-pyrrolidinyl)methanone (prepared from pyrrolidine and 5-fluoro-2H-3,1-benzoxazine-2,4(1H)-dione using the methods described in Example 17) and CMI were reacted using conditions described in the general procedure for CMI coupling to give {2-[(4,5-dihydro-1H-imidazol-2-ylmethyl)amino]-6-fluorophenyl}(1-pyrrolidinyl)methanone.

Example 42

{4-Chloro-2-[(4,5-dihydro-1H-imidazol-2-ylmethyl)amino]phenyl}(1-pyrrolidinyl)methanone 7-Chloro-2H-3,1-benzoxazine-2,4(1H)-dione was prepared from 2-amino-4-chlorobenzoic acid using the method described in Example 38.

(2-Amino-4-chlorophenyl)(1-pyrrolidinyl)methanone (prepared from pyrrolidine and 7-chloro-2H-3,1-benzoxazine-2,4(1H)-dione using the methods described in Example 17) and CMI were reacted using conditions described in the general procedure for CMI coupling to give (4-chloro-2-[(4,5-dihydro-1H-imidazol-2-ylmethyl)amino]phenyl}(1-pyrrolidinyl)methanone.

Example 43

{2-[(4,5-Dihydro-1H-imidazol-2-ylmethyl)amino]-4-methylphenyl}(1-pyrrolidinyl)methanone 7-Methyl-2H-3,1-benzoxazine-2,4(1H)-dione was prepared from 2-amino-4-methylbenzoic acid using the method described in Example 38.

(2-Amino-4-methylphenyl)(1-pyrrolidinyl)methanone (prepared from pyrrolidine and 7-methyl-2H-3,1-benzoxazine-2,4(1H)-dione using the methods described in Example 17) and CMI were reacted using conditions described in the general procedure for CMI coupling to give {2-[(4,5-dihydro-1H-imidazol-2-ylmethyl)amino]-4-methylphenyl}(1-pyrrolidinyl)methanone.

Example 44

2-[(4,5-Dihydro(1H-imidazol-2-ylmethyl)amino]-N',N'-dimethylbenzohydrazide hydrochloride Isatoic anhydride (5.0 g, 30.6 mmol), 35 mL of absolute ethanol and anhydrous 1,1-dimethylhydrazine (2.56 mL, 33.6 mmol) were refluxed for 2 hours. The volatiles were removed in vacuo. The residue was purified by silica gel flash chromatography using 5–10% methanol in dichloromethane. Concentration in vacuo produced 1.60 g of 2-aminobenzoic acid N',N'-dimethylhydrazide.

2-Aminobenzoic acid N',N'-dimethylhydrazide and CMI were reacted using conditions described in the general procedure for CMI coupling to give 2-[(4,5-dihydro-1H-imidazol-2-ylmethyl)amino]-N',N'-dimethylbenzohydrazide, isolated as the hydrochloride salt.

Example 45

N'-Acetyl-2-[(4.5-dihydro-1H-imidazol-2-ylmethyl)amino]benzohydrazide

Anthranilic acid N'-acetylhydrazide (prepared from acetic hydrazide and isatoic anhydride using the method described in Example 44) and CMI were reacted using conditions described in the general procedure for CMI coupling to give N'-acetyl-2-[(4,5-dihydro-1H-imidazol-2-ylmethyl)amino]benzohydrazide.

Example 46

N'-{2-[(4,5-dihydro-1H-imidazol-2-ylmethyl)amino]benzoyl}methanesulfonohydrazide 1-Anthaniloyl-2-methylsulfonyl) hydrazine (prepared from methanesulfonyl hydrazide (Lancaster Synthesis, Windham, N.H.) and isatoic anhydride using the method described in Example 44) and CMI were reacted using conditions described in the general procedure for CMI coupling to give N'-{2-[(4,5-dihydro-1H-imidazol-2-ylmethyl)amino]Benzoyl}methanesulfonohydrazide.

Example 47

2-[(4,5-Dihydro(1H-imidazol-2-ylmethyl)amino]-N'-(2,2,2-trifluoroethyl)benzohydrazide 2-Amino-N'-(2,2,2-trifluoroethyl)benzohydrazide (prepared from 2,2,2-trifluoroethylhydrazine and isatoic anhydride using the method described in Example 44) and CMI were reacted using conditions described in the general procedure for CMI coupling to give 2-[(4,5-dihydro-1H-imidazol-2-ylmethyl)amino]-N-(2,2,2-trifluoroethyl)benzohydrazide.

Example 48

2-[(4,5-Dihydro-1H-imidazol-2-ylmethyl)amino]-N'-morpholinobenzamide

2-Amino-N-morpholinobenzamide (prepared from 4-aminomorpholine and isatoic anhydride using the method described in Example 44) and CMI were reacted using conditions described in the general procedure for CMI coupling to give 2-[(4,5-dihydro-1H-imidazol-2-ylmethyl)amino]-N'-(morpholino)benzamide.

Example 49

N'-(tert-Butyl)-2-[(4.5-dihydro-1H-imidazol-2-ylmethyl)amino]benzohyhydrazide

2-Amino-N'-(tert-butyl)benzohydrazide (prepared from tert-butylhydrazine and isatoic anhydride using the method described in Example 44) and CMI were reacted using conditions described in the general procedure for CMI coupling to give N'-(tert-butyl)-2-[(4,5-dihydro-1H-imidazol-2-ylmethyl)amino]benzohydrazide.

Example 50

2-[(4.5-Dihydro-1H-imidazol-2-ylmethyl)amino]-N-methylbenzenesulfonamide fumarate To a solution of 2-nitrobenzenesulfonyl chloride (25 g, 0.113 mol) and dichloromethane (450 mL) at 4° C. was added dropwise 2M methylamine in tetrahydrofuran (68 mL). The mixture was stirred overnight allowing the ice bath to melt. More 2M methylamine in tetrahydrofuran (97 mL) was added and the reaction was stirred for 1 hour. The reaction mixture was concentrated in vacuo. The residue was dissolved in chloroform (500 mL) and was washed with saturated sodium bicarbonate (250 mL). The aqueous layer was extracted with chloroform (250 mL) and all the chloroform layers combined, dried over sodium sulfate and filtered. The filtrate was concentrated in vacuo and the residue purified by silica gel chromatography using 0–4% methanol in dichloromethane. 22.63 g of N-methyl-2-nitrobenzenesulfonamide was obtained.

N-Methyl-2-nitrobenzenesulfonamide (1.0 g, 4.6 mmol), 10% palladium on carbon (100 mg) and absolute ethanol (30 mL) were placed in a Parr bottle, the bottle placed on a Parr apparatus under a hydrogen atmosphere (45 psi), and shaken for 1 hour, The Parr bottle was evacuated and flushed with nitrogen, then the mixture was filtered through a disposable syringe filter. The filtrate was concentrated in vacuo to yield 0.81 g of 2-amino-N-methylbenzenesulfonamide.

2-Amino-N-methylbenzenesulfonamide was treated with CMI using the general methods described in Example 1 to provide 2-[(4,5-dihydro-1H-imidazol-2-ylmethyl)amino)-N-methylbenzenesulfonamide as the fumarate salt.

$^1$H NMR (400 MHz, DMSO-$d_6$) δ 7.57 (dd, $J_{AB}$=1.4 Hz, $J_{AC}$=7.9 Hz,1H); 7.42 (dd, J=7.6 Hz, 7.6 Hz, 1H); 6.79 (dd, J=7.5 Hz, J=7.5 Hz, 1H) 6.74 (d, J=8.4 Hz, 1H); 6.52 (t, J=5.8 Hz, 1H); 6.45 (s, 2H); 4.26 (d, J=5.8 Hz, 2H); 3.70 (s, 4H); 2.33 (s, 3H). Mass. Spec. 269 (100%) (M+H); 199 (100) (M+H−70).

Example 51

2-[(4, 5-Dihydro N-imidazol-2-ylmethyl)amino]-N-ethylbenzenesulfonamide fumarate 2-Amino-N-ethylbenzenesulfonamide (prepared from 2-nitrobenzenesulfonyl chloride and ethylamine using the methods described in Example 50) and CMI were reacted using conditions described in the general procedure for CMI coupling to give 2-[(4,5-dihydro-1H-imidazol-2-ylmethyl)amino]-N-ethylbenzenesulfonamide, isolated as the fumarate salt.

$^1$HMR (400 MHz, DMSO-$d_6$) δ 7.59 (dd, $J_{AB}$=1.4 Hz, $J_{AC}$=7.9 Hz,1H); 7.41 (dd, J=7,5 Hz, J=7.5 Hz, 1H); 6.78 (m, 2H); 6.48 (m, 3H); 4.25 (d, J=5.8 Hz, 2H); 3.7 (s, 4H); 2.70 (q, J=7.2 Hz, 2H); 0.90 (t, J=7.1 Hz, 3H). Mass. Spec. 283 (90%) (M+H); 213 (100%) (M+H−70).

Example 52

Cyclopentyl{2-[(4,5-dihydro-1H-imidazol-2-ylmethyl)amino}phenyl)methanone hydrochloride Anthranilonitrile (2.6 g, 22 mmol) in diethyl ether (30 mL) was added dropwise to cyclopentylmagnesium chloride (33 mL of a 2M solution in diethyl ether) in diethyl ether (95 mL) at room temperature, under a nitrogen atmosphere. The mixture was heated to reflux, and maintained for 1 hour. The mixture was cooled to 0° C., and deionized water (10 mL) was added dropwise over 30 minutes (caution: extremely exothermic). After stirring for 15 minutes, 15% aqueous sulfuric acid (75 mL) was added slowly. After stirring for 15 minutes, the mixture was heated to reflux and maintained for 1 hour, The mixture was cooled and portioned. The aqueous portion was washed with ethyl acetate (2×50 mL). The organic extracts were combined, washed with dilute potassium carbonate solution, washed with saturated sodium chloride solution, dried over sodium sulfate, and the volatiles removed by evaporation under reduced pressure to yield 3.77 g of (2-aminophenyl)(cylclopentyl)methanone.

(2-Aminophenyl)(cylclopentyl)methanone and CMI were reacted using conditions described in the general procedure for CMI coupling to give cyclopentyl {2-[(4,5-dihydro-)-1H-imidazol-2-ylmethyl)amino]phenyl}methanone, isolated as the hydrochloride salt.

Example 53

1-{2-[(4,5-Dihydro-1H-imidazol-2-ylmethyl)amino]phenyl}-1-pentanone.

1-(2-Aminophenyl)-1-pentanone (prepared from anthranilonitrile and butylmagnesium chloride using the method described in Example 52) and CMI were reacted using conditions described in the general procedure for CMI coupling to give 1-{2-[(4,5-dihydro-1H-imidazol-2-ylmethyl)amino]phenyl}-1-pentanone.

Example 54

1-{2-[(4.5-Dihydro-1H-imidazol-2-ylmethyl)amino]phenyl}-1-butanone 1-(2-Aminophenyl)-1-butanone (prepared from anthranilonitrile and propylmagnesium chloride using the method described in Example 52) and CMI were reacted using conditions described in the general procedure for CMI coupling to give 1-{2-[(4,5-dihydro-1H-imidazol-2-ylmethyl)amino]phenyl}1-butanone.

Example 55

1-{2-[(4;5-Dihydro-1H-imidazol-2-ylmethyl)amino]phenyl}-2-ethyl-1-butanone 1-(2-Aminophenyl)-2-ethyl-1-butanone (prepared from anthranilonitrile and 1-ethylpropylmagnesium bromide [prepared from 3-bromopentane and magnesium turnings] using the method described in Example 52) and CMI were reacted using conditions described in the general procedure for CMI coupling to give 1-{2-[(4,5-dihydro-1H-imidazol-2-ylmethyl)amino]phenyl}-2-ethyl-1-butanone.

Example 56

1-{2-[(4,5-Dihydro-1H-imidazol-2-ylmethyl)amino]phenyl}-4-penten-1-one hydrochloride 1-(2-Aminophenyl)-4-penten-1-one (prepared from anthranilonitrile and 3-butenylmagnesium bromide using the method described in Example 52) and CMI were reacted using conditions described in the general procedure for CMI coupling to give 1-{2-[(4,5-dihydro-1H-imidazol-2-ylmethyl)amino]phenyl}-4-penten-1-one, isolated as the hydrochloride salt.

Example 57

1-{2-[(4,5-Dihydro-1H-imidazol-2-ylmethyl)amino]phenyl}-1-ethanone hydrochloride 2'-Aminoacetophenone and CMI were reacted in ethanol using conditions described in the general procedure for CMI coupling to give 1-{2-[(4,5-dihydro-1H-imidazol-2-ylmethyl)amino]phenyl}-1-ethanone as the hydrochloride salt.

$^1$H NMR (400 MHz; DMSO-d$_6$): δ 2.56 (s, 3H), 3.79 (s, 4H), 4.43 (d, J=6.3 Hz, 2H), 6.62 (d, J=8.5 Hz, 1H), 6.74 (dd, J=7.5 Hz, 7.5 Hz, 1H), 7.42 (dd, J=7.8 Hz, 7.8 Hz; 1H), 7.91 (d, J=7.9 Hz, 1H), 8.96 (br t, J=6.2 Hz, 1H), 10.00 (br s, 2H). Mass. Spec. 218 (100%) (M+H).

Example 58

1-{2-(4,5-Dihydro-1H-imidazol-2-ylmethyllamino] phenyl}-1-propanone hydrochloride 1-(2-Aminophenyl)-1-propanone (prepared from anthranilonitrile and ethylmagnesium bromide using the method described in Example 52) and CMI were reacted using conditions described in the general procedure for CMI coupling to give 1-{2-[(4,5-dihydro-1H-imidazol-2-ylmethyl)amino]phenyl}-1-propanone as the hydrochloride salt.

Example 59

(E)-1-{2-[(4.5-Dihydro-1H-imidazol-2-ylmethyl) amino]phenyl}-1-ethanone O-methyloxime To a 250-mL rotted bottom flask were added 2'-aminoacetophenone (3.0 g, 22.2 mmol), methoxylamine hydrochloride (2.0 g, 24.4 mmol, 1.1 eq) and ethanol (30 mL). The reaction mixture was heated at reflux with stirring under a nitrogen atmosphere for 3 h. The oil bath was removed and the reaction mixture was allowed to cool at room temperature. The reaction mixture was filtered and the filtered solid was washed with ethanol followed by diethyl ether to give 0.64 g of 1-(2-aminophenyl)-1-ethanone O-methyloxime hydrochloride as a white solid.

1-(2-Aminophenyl)-1-ethanone O-methyloxime and CMI were reacted using conditions described in the general procedure for CMI coupling to give (E)-1-{2-[(4,5-dihydro-1H-imidazol-2-ylmethyl)amino]phenyl}-1-ethanone-O-methyloxime.

Example 60

(E)-1-{2-[(4,5-Dihydro-1H-imidazol-2-ylmethyl) amino]phenyl}-1-ethanone O-ethyloxime 1-(2-Aminophenyl)-1-ethanone O-ethyloxime (prepared from 2'-aminoacetophenone and O-ethylhydroxylamine hydrochloride using the method described in Example 59) and CMI were reacted using conditions described in the general procedure for CMI coupling to give (E)-1-{2-[(4,5-dihydro-1H-imidazol-2-ylmethyl)amino]phenyl}-1-ethanone O-ethyloxime.

Example 61

(E)-2-[(4,5-Dihydro-1H-imidazol-2-ylmethyl)amino] benzaldehyde O-methyloxime

To a 250-ml, round bottom flask were added 2-nitrobenzaldehyde (5.0 g, 33.1 mmol); methoxylamine hydrochloride (3.0 g, 35.9 mmol, 1.09 eq), and ethanol (50 mL). The reaction mixture was heated at reflux with stirring under a nitrogen atmosphere for 3 h and then allowed to stand at room temperature overnight. The reaction mixture was concentrated in vacuo to give a yellow solid. The crude product was partitioned between dichloromethane and water. The layers were separated and the organic phase was washed with water followed by saturated sodium chloride. The organic phase was dried over magnesium sulfate, filtered and the filtrate was concentrated in vacuo to give 5.46 g of (E)-O-methyloxime-2-nitrobenzaldehyde.

To a 300-mL round bottom flask were added (E)-O-methyloxime-2-nitrobenzaldehyde (2.0 g, 11.1 mmol) and 1,4-dioxane (25 mL). The stirred mixture was heated at 80° C. A solution of sodium sulfide nonahydrate (6.0 g, 25 mmol, 2.25 eq) in water (25 mL) was heated at 80° C. and then added to the hot solution of (E)-O-methyloxime-2-nitrobenzaldehyde. The reaction mixture was heated between 65° C. and 90° C. for 45 min. The oil bath was removed and the reaction mixture was allowed to cool at room temperature. To the reaction mixture was added water (25 mL) and heating was resumed at 95° C. for 2 h. A solution of sodium sulfide nonahydrate (6.0 g, 25 mmol, 2.25 eq) in water (15 mL) was heated at 70° C. and then added to the reaction mixture which was at 80° C. The reaction mixture was heated at 85° C. for 15 min. The oil bath was removed and the reaction mixture was allowed to cool at room temperature. The reaction mixture was extracted with dichloromethane and the layers were separated. The organic phase was washed with saturated sodium chloride, dried over magnesium sulfate, filtered, and the filtrate was concentrated in vacuo to give 1.31 g of the crude product. The crude product was purified by column chromatography over silica gel with hexanes:ethyl acetate (3:1) as eluent to give 0.73 g of (E)-O-methyloxime-2-aminobenzaldehyde as a yellow liquid.

(E)-O-Methyloxime-2-aminobenzaldehyde and CMI were reacted using conditions described in the general procedure for CMI coupling to give (E)-2-[(4,5-dihydro-1H-imidazol-2-ylmethyl)amino]benzaldehyde O-methyloxime.

Example 62

(E)-1-{2-[(4,5-Dihydro-1H-imidazol-2-ylmethyl) amino]phenyl}-1-propanone O-methyloxime hydrochloride To a 100-mL round bottom flask were added 1-(2-aminophenyl)-1-propanone (1.11 g, 7.44 mmol, prepared in Example 58), methoxylamine hydrochloride (0.7 g, 8.38 mmol, 1.13 eq), and ethanol (15 mL). The reaction mixture was heated at reflux with stirring under a nitrogen atmosphere for 3 h. The oil bath was removed and the reaction mixture was allowed to stand at mom temperature for approximately three weeks. The reaction mixture was concentrated in vacuo and the nude product was partitioned between dichloromethane and saturated sodium bicarbonate. The layers were separated and the organic phase was dried over magnesium sulfate, filtered, and the filtrate was concentrated in vacuo to give 1.24 g of an orange oil. The crude product was purified by column chromatography over silica gel with hexanes:ethyl acetate (8:1) as eluent to give 0.90 g of (E)-1-(2-aminophenyl)-1-propanone O-methyloxime and 0.31 g of (Z)-1-(2-aminophenyl)-1-propanone O-methyloxime.

(E)-1-(2-Aminophenyl)-1-propanone O-methyloxime and CMI were reacted using conditions described in the general procedure for CMI coupling to give (E)-1-{2-[(4,5-dihydro-1H-imidazol-2-ylmethyl)amino]phenyl}-1-propanone O-methyloxime as the hydrochloride salt.

Example 63

(Z)-1-{2-[(4,5-Dihydro-1H-imidazol-2-ylmethyl) amino]phenyl}-1-propanone O-methyloxime hydrochloride (Z)-1-(2-Aminophenyl)-1-propanone O-methyloxime (prepared in Example 62) and CMI were reacted using conditions described in the general procedure for CMI coupling to give (Z)-1-{2-[(4,5-dihydro-1H-imidazol-2-ylmethyl)amino]phenyl}-1-propanone O-methyloxime as the hydrochloride salt

Example 64

N-(4,5-dihydro-1H-imidazol-2-ylmethyl)-2-(1-pyrrolidinyl)aniline

[<b]old2-Fluoronitrobenzene (2.82 g, 20 mmol) was mixed with pyrrolidine (1.56 g, 22 mmol), and potassium carbonate (5.5 g, 40 mmol) in DMF (10 mL). After beating for 16 hours, the mixture was filtered and the filtrate evaporated in vacuo to an oil. This oil was treated with water (10 mL) and dichloromethane (100 mL). The organic phase was collected, dried ($MgSO_4$), filtered, and evaporated to give 1-(2-nitrophenyl)pyrrolidine (0.5 g). The crude product was reduced using 5% palladium on carbon (0.1 g) in ethanol (30mL) and hydrogen at 40 psi for 2 hours. The solution was filtered through celite to remove catalyst and the filtrate evaporated in vacuo to give 2-(1-pyrrolidino) aniline (0.33 g). The crude product was coupled with CMI, under conditions described in the general procedure for CM couplings, to give N-(4,5-dihydro-1H-imidazol-2-ylmethyl)-2-(1-pyrrolidinyl)aniline.

Example 65

N-1-(sec-Butyl)-N-2-(4,5-dihydro-1H-imidazole-2-ylmethyl) -1,2-benzenediamine

Under conditions similar to those used for the preparation of N-(4,5-dihydro-1H-imidazol-2-ylmethyl)-2-(1-pyrrolidinyl)aniline (Example 64), sec-butylamine was reacted with 2-fluoronitrobenzene, the nitro group was reduced, and the aniline was coupled with CMI to give N-1-(sec-butyl)-N-2-(4,5-dihydro-1H-imidazole-2-ylmethyl)-1,2-benzenediamine.

Example 66

N-1-(4,5-dihydro-1H-imidazol-2-ylmethyl)-N-2-isobutyl-1,2-benzenediamine

Under conditions similar to those used for the preparation of N-(4,5-dihydro-1H-imidazol-2-ylmethyl)-2-(1-pyrrolidioyl)aniline (Example 64), iso-butylamine was reacted with 2-fluoronitrobenzene, the nitro group was reduced, and the aniline was coupled with CMI to give N-1-(4,5-dihydro-1H-imidazol-2-ylmethyl)-N-2-isobutyl-1, 2-benzenediamine.

Example 67

2-(1-Azepinyl)-N-(4,5 dihydro-1H-imidazol-2-ylmethyl]aniline

Under conditions similar to those used for the preparation of N-(4,5-dihydro-1H-imidazol-2-ylmethyl)-2-(1-pyrrolidinyl)aniline (Example 64), hexamethyleneimine was reacted with 2-fluoronitrobenzene, the nitro group was reduced and the aniline was coupled with CMI to give 2-(1-azepinyl)-N-(4,5-dihydro-1H-imidazol-2-ylmethyl) aniline .

Example 68

N-(4,5-Dihydro-1H-imidazol-2-ylmethyl)-2-(1-piperidinyl)aniline

Under conditions similar to those used for the preparation of N-(4,5-dihydro-1H-imidazol-2-ylmethyl)-2-(1-pyrrolidinyl)aniline (Example 64), piperidine was reacted with 2-fluoronitrobenzene, the nitro group was reduced, and the aniline was coupled, with CMI to give N-(4,5-dihydro-1H-imidazol-2-ylmethyl)-2-(1-piperidinyl) aniline.

Example 69

N-1-(4,5-Dihydro-1H-imidazol-2-ylmethyl)-N-2-ethyl-N-2-propyl-1,2-benzenediamine Under conditions similar to those used for the preparation of N-(4,5-dihydro-1H-imidazol-2-ylmethyl)-2-(1-pyrrolidinyl)aniline (Example 64), N-ethyl-N-propylamine was reacted with 2-fluoronitrobenzene, the nitro group was reduced and the aniline was coupled with CMI to give N-1-(4,5-dihydro-1H-imidazol-2-ylmethyl)-N-2-ethyl-N-2-propyl-1,2-benzenediamine.

Example 70

N-(4,5-Dihydro-1H-imidazol-2-ylmethyl)-2'-methyl [1,1'-biphenyl]-2-amine fumarate 2-Methyl-2'-nitrobiphenyl (2.09 g, 9.8 mmol; prepared as described by Snieckus: *Synthesis*, 1989, 184–188) was reduced as in Example 64, and purified by column chromatography to give 1.64 g of 2-amino-2'-methylbiphenyl. 2-Amino-2'-methylbiphenyl (1.01 g, 5.52 mmol) and CMI (0.428 g, 2.76 mmol) were coupled using the general procedures outlined in Example 1 to give N-(4,5-dihydro-1H-imidazol-2-ylmethyl)-2'-methyl[1,1'-biphenyl]-2-amine as a fumarate salt.

Example 71

N-(4,5-Dihydro-1H-imidazol-2-ylmethyl)-2'-methoxy[1,1'-biphenyl]-2-amine fumarate 2-Methoxy-2'-nitrobiphenyl was prepared, the nitro group reduced to the amine, and the resulting 2-amino-2'-methoxybiphenyl reacted with CMI using the procedures described in Example 70 to produce 0.470 g of N-(4,5-dihydro-1H imidazol-2-ylmethyl)-2'-methoxy[1,1'-biphenyl]-2-amine as the fumarate salt.

Example 72

N-(4,5-Dihydro-1H-imidazol-2-ylmethyl-3'-methyl [1,1'-biphenyl]-2-amine fumarate 3-Methyl-2'-nitrobiphenyl was prepared, the nitro group reduced to the amine, and the resulting 2-amino-3'-methylbiphenyl reacted with CMI using the procedures described in Example 70 to produce 0.120 g of N-(4,5-dihydro-1H-imidazol-2-ylmethyl)-3'-methyl[1,1'-biphenyl]-2-amine as the fumarate salt.

Example 73

N-(2'-Chloro[1,1'-biphenyl]-2-yl)-N-(4,5-dihydro-1H-imidazol-2-ylmethyl)amine fumarate 2-Chloro-2'-nitrobiphenyl was prepared, the nitro group reduced to the amine, and the resulting 2-amino-2'-chlorobiphenyl reacted with CMI using the procedures described in Example 70 to produce 0.110 g N-(2'-chloro [1,1'-biphenyl]-2-yl)-N-(4,5-dihydro-1H-imidazol-2-ylmethyl)amine as the fumarate salt.

Example 74

N-(4,5- Dihydro-1H-imidazol-2-ylmethyl)-2-thienyl)aniline hydrochloride

2-Nitroiodobenzene (1.0 g, 4.0 mmol) was dissolved in DMF (25 mL), treated with bis(triphenylphosphine)

palladium(II) chloride (0.1 g) and 2-tributylstannylthiophine (1.65 g, 4.4 mmol) and heated at 100° C. under nitrogen overnight. After concentration in vacuo, the residue was taken up in ether, washed with deionized water and saturated sodium chloride solution, dried over magnesium sulfate and evaproated. The oil was purified by silica gel chromatography using ethyl acetate and hexanes. Concentration in vacuo produced 500 mg of 2-(2-nitrophenyl)thiopyene, which was reduced as in Example 64 to give 336 mg of 2-(2-aminophenyl)thiophene.

2-(2-Aminophenyl)thione (0.330 g, 1.9 mmol) and CMI (0.200 g 1.3 mmol) were coupled under conditions described inthe general method for CMI couplings to give 210 mg of N-(4,5dihydro--1H-imidazol-2-ylmethy)-2-(2-thienyl) aniline hydrochloride.

Example 75

N-(4,5-Dihydro-1H-imidazol-2-ylmethyl)-2-(2-pyrazinyl)aniline (2-Trimethylstannyl-phenyl)-carbamic acid tert-butyl ester (*Bioorganic & Medicinal Chemistry*, 1998, 6,811–823) (1.4 g, 3.93 mmol), 2-chloropyrazine (0.5 g, 4.33 mmol, 1,1 eq), tetrakis(triphenylphosphine)palladium (0.18 g, 0.156 mmol), and copper (I) b (0.022 g, 0.156 mmol), in 1,4-dioxane (10 mL) were heated at 110° C. for 75 min. The reaction mixture was allowed to cool at room temperature. The crude product was adsorbed onto silica gel and purified by column chromatography to give 0.65 g of tert-butyl 2-(2-pyrazinyl)phenylcarbamate.

To tert-butyl 2-(2-pyrazinyl)phenylcarbamate (0.62 g, 2.29 mmol), dichloromethane (10 mL), and anisole (1 mL) was added trifluoroacetic acid (10 mL). The reaction mixture was stirred at room temperature under a nitrogen atmosphere for 4 h and allowed to stand at room temperature overnight. The reaction mixture was concentrated in vacuo to give 0.41 g of 2-(2-pyrazinyl)aniline, which was coupled with CMI (0.20 g, 1.3 mmol), under conditions described in the general procedure for CMI couplings, to give 0.022 g of N-(4,5-dihydro-1H-imidazol-2-ylmethyl)-2-(2-pyrazinyl)aniline.

$^1$H NMR (300 MHz; DMSO-$d_6$): δ 3.42 (br s, 4H), 3.84 (d, J=4.7 Hz, 2H), 6.70 (m, 2H), 7.28 (dd, J=7.7 Hz, 7.7 Hz, 1H), 7.70 (d, J=7.6 Hz, 1H), 8.20 (m, 1H), 8.52 (m, 1H), 8.61 (br s, 1H), 9.09 (br s, 1H). Mass. Spec. 254 (70%) (M+H).

Example 76

N-(4,5-Dihydro-1H-imidazol-2-ylmethyl)-2-(1-methyl-1H-pyrrol-2-yl)aniline fumarate 2-Lithio-1-methylpyrrole was prepared as described in *Tetrahedron Lett.*, 1981, 22, 5319 and treated with dimethyltin chloride to give, after workup, 1-methyl-2-(trimethylstannyl)-1H-pyrrole.

1-Methyl-2-(trimethylstannyl)-1H-pyrrole (3.94 g, 14.7 mmol) and 1-bromo-2-nitrobenzene (3.22 g, 15.9 mmol, 1.08 eq) were coupled as in Example 75 to give 2.04 g of 1-methyl-2-(2-nitrophenyl)-1H-pyrrole, which was reduced as in Example 64 to give 1.53 g of 2-(1-methyl-1H-pyrrol-2-yl)aniline.

CMI (0.25 g, 1.61 mmol) and 2-(1-methyl-1H-pyrrol-2-yl)aniline (0.56 g, 3.25 mmol, 2.0 eq) were reacted under conditions described in the general procedure for CMI couplings to give 0.035 g of N-(4,5-dihydro-1H-imidazol-2-ylmethyl)-2-(1-methyl-1H-pyrrol-2-yl)aniline fumarate.

$^1$H NMR (300 MHz; DMSO-$d_6$): δ 3.40 (s, 3H), 3.68 (s, 4H), 4.06 (d, J=5.6 Hz, 2H), 5.24 (br t, J=5.8 Hz, 1H), 6.08 (m,1H), 6.12 (m, 1H), 6.41 (s, 2H), 6.55 (d, J=8.1 Hz, 1H), 6.71 (dd, J=7.3 Hz, 7.3 Hz, 1H), 6.85 (m, 1H), 7.03 (d, J=7.4 Hz, 1H), 7.18 (dd, J=7.4 Hz, 7.4 Hz, 1H). Mass. Spec. 255 (25%) (M+H).

Example 77

N-(4,5-Dihydro-1H-imidazol-2-ylmethyl)-2-(1-ethyl-1H-pyrrol-2-yl)aniline fumarate Under conditions analogous to Example 76, 2-(1-ethyl-1H-pyrrol-2-yl)aniline was prepared and coupled with CMI to give N-(4,5-dihydro-1H-imidazol-2-ylmethyl)-2-(1-ethyl-1H-pyrrol-2-yl)aniline as the fumarate salt.

$^1$H NMR (300 MHz; DMSO-$d_6$); δ 1.10 (t, J=7.2 Hz, 3H), 3.69 (m, 6H), 4.05 (d, J=5.6 Hz, 2H), 5.15 (br t, J=5.8 Hz, 1H), 6.09 (m, 2H), 6.41 (s, 2H), 6.55 (d, J=8.1 Hz, 1H), 6.70 (dd, J=7.4 Hz, 7.4 Hz, 1H), 6.90 (m, 1H), 6.99 (d, J=7.3 Hz, 1H), 7.18 (dd, J=7.5 Hz, 7.5 Hz, 1H). Mass. Spec. 269 (15%) (M+H).

Example 78

N-(4,5-Dihydro-1H-imidazole-2-ylmethyl)-2-(1,5-dimethyl-1H-pyrrol-2-yl)aniline fumarate 1-Methyl-2-pyrrole carboxaldehyde (11.5 g, 106 mmol), hydrazine hydrate (55% aqueous solution) (32.0 mL, 32.9 g, 565 mmol, 5.3 eq), and ethylene glycol (85 mL) were heated at 145° C. for 1–2 h. as the water distilled from the reaction mixture. The oil bath was removed and the reaction mixture was allowed to cool to 60° C. The distillation head was replaced with a reflux condenser. To the reaction mixture was added potassium hydroxide (21.0 g, 375 mmol) and the reaction mixture was heated at 130° C. for approximately 1 h until nitrogen evolution had ceased. The oil bath was removed and the reaction mixture was allowed to cool at room temperature. The reaction mixture was extracted with diethyl ether (3×50 mL). The diethyl ether extracts were combined, dried over magnesium sulfate, filtered and the filtrate was concentrated in vacuo to give 10.45 g of the crude product. The product was purified by distillation. The 1,2-dimethyl-1H-pyrrole was collected at 140–144° C. (4.86 g).

Under conditions analogous to Example 76, 2-(1,5-Dimethyl-1H-pyrrol-2-yl)phenylamine was prepared and coupled with CMI to give 0.077 g of N-(4,5-dihydro-1H-imidazol-2-ylmethyl)-2-(1,5-dimethyl-1H-pyrrol-2-yl) aniline fumarate.

Example 79

N-(4.5-Dihydro-1H-imidazol-2-ylmethyl)-2-(3-methyl-2-pyridinyl)aniline fumarate

2-Bromo-3-methylpyridine (0.65 g, 3.8 mmol) and N-(tert-butoxycarbonyl)-2-amino-1-phenylboronic acid (0.90 g, 3.8 mmol), prepared according to the method described by J. J. S. Lambda and J. M. Tour in *J. Am. Chem. SDC.*, 1994,116,11723–11736, were coupled as in Example 70 (also see *J. Org. Chem.*, 1995, 60, 292), to give 1.43 g of crude tert-butyl 2-(3-methyl-2-pyridinyl)phenylcarbamate, which was deprotected as in Example 75 to give 0.45 g of 2-(3-methyl-2-pyridinyl)aniline.

CMI (91%) (0.28 g, 1.64 mmol) and 2-(3-methyl-2-pyridinyl)aniline (0.435 g, 2.36 mmol, 1.4 eq) were coupled as described in the general procedure for CMI couplings to give 0.107 g of N-(4,5-dihydro-1H-imidazol-2-ylmethyl 2-(3-methyl-2-pyridinyl)aniline fumarate.

Example 80

N-(4,5-Dihydro-1H-imidazol-2-ylmethyl)-2'-(trifluoromethyl)[1,1'-biphenyl]-2-amine fumarate 2-Nitro-2'-(trifluoromethyl)biphenyl was prepared analogously to Example 70, the nitro group was reduced to the amine, and the resulting 2'-(trifluoromethyl)-[1'-biphenyl]-2-amine was coupled with CMI to give N-(4,5-dihydro-1H-imidazol-2-ylmethyl)-2'-(trifluoromethyl)[1,1'-biphenyl]-2-amine fumarate.

Example 81

N-(4,5-Dihydro-1H-imidazol-2-ylmethyl)-3-methyl-2-thienyl)aniline fumarate

2-Bromo-3-nitrotoluene (3.35 g, 15.5 mmol) and 2-(tributylstannyl)-thiophene (5.7 g, 15.3 mmol, 1.0 eq) were coupled as in Example 75 to give 2.08 g of 2-(2-methyl-6-nitrophenyl)thiophene, which was reduced under conditions similar to Example 64 to give 1.4 g of 3-methyl-2-(2-thienyl)aniline.

CMI (91%) (0.307 g, 1.90 mmol) and 3-methyl-2-(2-thienyl)aniline (0.709 g, 3.75 mmol, 2.05 eq) were reacted under conditions described in the general procedure for CMI coupling to give 0.081 g of N-(4,5-dihydro-1H-imidazol-2-ylmethyl)-3-methyl-2-(2-thienyl)aniline fumarate.

Example 82

N-(4,5-Dihydro-1H-imidazol-2-ylmethyl)-2-(2-furyl)aniline hydrochloride.

A DMF solution of 2-nitrobromobenzene (2.02 g), 2-tributylstannylfuran (3.31 mL), and tetrakis (triphenylphosphine)palladium was heated at 97° C. under $N_2$ overnight. The mixture was evaporated to a small volume. The residue was suspended in 40 mL of water. This mixture was extracted with two 50 mL portions of $Et_2O$. The combined extracts were dried and evaporated. This oil was purified by chromatography on silica gel with 10% EtOAc/hexanes to yield 0.51 g (27%) of 2-(2-nitrophenyl)furan. [This compound was reported in Smith et al.; J. Am. Chem. Soc. 1953, 75, 6335.]

2-(2-Nitrophenyl)furan (0.51 g) was dissolved in 10 mL of EtOH. To this solution was added 0.07 g of 10% Pd/C and 1 mL of EtOH. This mixture was stirred and treated dropwise with 1.4 mL of 35% hydrazine. The suspension was filtered, and the filtrate was evaporated. The resulting residue was taken up in 50 mL of toluene and re-evaporated to give 2-(2-aminophenyl)furan. [This compound was reported in Smith et al.; J. Am. Chem Soc. 1953, 75, 6335.]

2-(2-Aminophenyl)tan (0.43 g) and CM (0.38 g) were reacted under conditions described in the general procedure for CMI couplings to afford 0.093 g of N-(4,5-dihydro-1H-imidazol-2-ylmethyl)-2-(2-furyl)aniline hydrochloride.

Example 83

N-(4,5-Dihydro-1H-imidazol-2-ylmethyl)-2-(2-pyridinyl)aniline hydrochloride.

A solution of 2-nitrobromobenzene (2.02 g), 2-bromopyridine (0.80 g), copper powder (1.29 g), and palladium dichloride (0.049 g) in 15 mL of DMSO was heated at 120° C. under $N_2$ for 2 hours. Once cooled, the mixture was diluted with 100 mL of 10% aqueous ammonia and stirred for 30 min. This mixture was filtered, and the filtrate was extracted several times with $CHCl_3$. The combined extracts were dried ($Na_2SO_4$) and evaporated. The crude product was purified by chromatography on silica gel with 20% EtOAc/hexanes to yield 0.12 g (22%) of 2-(2-Nitrophenyl)pyridine. [This compound was reported by Molina, Pedro; Lorenzo, Angeles; Aller, Enrique; *Tetrahedron*; 1992, 48, (22), 4601–4616.]

2-(2-Nitrophenyl)-pyridine (0.22 g) was reduced under conditions similar to Example 82 to give the aniline. [This compound was previously reported by Petrow et al.; J. Chem. Soc., 1943, 316.]

2-(2-Aminophenyl)pyridine (0.44 g) and CMI (0.4 g) were coupled under conditions described in the general procedure for CMI couplings to give N-(4,5-dihydro-1H-imidazol-2-y(methyl)-2-(2-pyridinyl)aniline hydrochloride.

Example 84

N-(4,5-Dihydro-1H-imidazol-2-ylmethyl)-2-(2-pyrimidinyl)aniline.

2-Nitrobromobenzene (2.02 g) and 2-bromopyrimidine (0.80 g) were coupled as in Example 83, and the product reduced as in Example 64 to give 2-(2-aminophenyl)pyrimidine. This was reacted with CMI under conditions described in the general procedure for CMI couplings to give N-(4,5-dihydro-1H-imidazol-2-ylmethyl)-2-(2-pyrimidinyl)aniline.

Example 85

N-(4.5-Dihydro-1H-imidazol-2-ylmethyl)-2-(3-trifluoromethyl-2-pyridyl)aniline fumarate Under conditions analogous to Example 79, N-(tert-butoxycarbonyl)-2-(3-trifluoromethyl-2-pyridyl)aniline was prepared, deprotected and coupled with CMI to afford the fumaric acid salt of N-(4,5-dihydro-1H-imidazol-2-ylmethyl)-2-(3-trifluoromethyl-2-pyridyl)aniline.

Example 86

N-(4,5-Dihydro-1H-imidazol-2-ylmethyl)-2-(2-methyl-1,3-oxazol-5-yl)aniline hydrochloride 2-Bromo-2'-nitroacetophenone (2.69 g, 11.0 mmol) in acetonitrile (20 mL) was cooled to 0° C. under nitrogen and treated with tetrabutylammonium azide (3.29 g, 11.6 mmol, TCI America, Portland, Oreg.) in acetonitrile (20 mL) dropwise. After stirring at room temperature for 30 minutes, the solution was poured into ice water (100 mL) and extracted with diethyl ether (3×30 mL). The extracts were combined, dried over magnesium sulfate, and the volatiles were removed by evaporation under reduced pressure to yield 2.19 g of 2-azido-2'-nitroacetophenone.

Triphenylphosphine, polymer bound, (5.3 g, 3 mmol/g, Fluka Chimica, Buchs, Switzerland) was scurried in toluene (75 mL). A solution of 2-azido-2'-nitroacetophenone (2.18 g, 10.6 mmol) and acetyl chloride (0.848 g, 10.8 mmol) in toluene (25 mL) was added at room temperature, under a nitrogen atmosphere. The solution was stirred at room temperature for six hours, then filtered over celite. All volatiles were removed from the filtrate by evaporation under reduced pressure to yield 0.91 g of crude 2-methyl-5-(2-nitrophenyl)oxazole. Crude 2-methyl-5-(2-nitrophenyl)oxazole (0.905 g, 4.44 mmol) was reduced as in Example 64, and the product purified by silica chromatography to give 0.51 g of 5-(2-aminophenyl)-2-methyloxazole.

5-(2-Aminophenyl)-2-methyloxazole (0.400 g, 2.3 mmol) and CMI (0.204 g, 1.32 mmol) were coupled as described in the general procedure for CMI couplings to give 0.045 g of N-(4,5-dihydro-1H-imidazol-2-ylmethyl)-2-(2-methyl-1,3-oxazol-5-yl)aniline as the hydrochloride salt.

Example 87

N-(4,5-Dihydro-1H-imidazol-2-ylmethyl)-2-(2-methyl-1,3-thiazol-4-yl)aniline hydrochloride 2-Bromo-2'-nitroacetopenone (1.15 g, 5.13 mmol) and thioacetamide (0.395 g, 5.26 mmol) were mixed in chloroform (10 mL) and tetrahydrofuran (5 mL), under nitrogen. The slurry was heated to reflux for 20 minutes, then cooled to room temperature, and 1.3 g of white solid collected by filtration. 1.2 g of the precipitate was dissolved in ethanol (50 mL), and heated to reflux for 1 hour. The solution was cooled to room temperature, and potassium carbonate (0.7 g) was added. The volatiles were removed by evaporation under reduced pressure. The residue was purified by silica gel chromatography using 20% ethyl acetate in hexanes to yield 0.53 g of 2-methyl-4-(2-nitrophenyl)thiazole, which was reduced as in Example 64, using platinum oxide hydrate as catalyst, to give 0.415 g of 4-(2-aminophenyl)-2-methylthiazole.

4-(2-Aminophenyl)-2-methylthiazole (0.375 g, 1.97 mmol) and CMI (0.153 g, 0.99 mmol) were coupled under conditions described in the general procedure for CMI couplings to give N-(4,5-dihydro-1H-imidazol-2-ylmethyl)-2-(2-methyl-1,3-thiazol-4-yl)aniline as the hydrochloride salt.

$^1$H NMR (300 MHz, DMSO-$d_6$) δ 10.08 (br s, 2H); 7.83 (s, 1H); 7.60 (d, J=7.4 Hz, 1H); 7.20 (dd, $J_1$=7.5 Hz, $J_2$=7.5 Hz, 1H); 6.76 (dd, $J_1$=7.5 Hz, $J_2$=7.5 Hz, 1H); 6.53 (d, J=8.1 Hz, 1H); 4.37 (br s, 2H); 3.81 (s, 4H); 2.75 (s, 3H). Mass. Spec. 273 (82%) (M+H); 203 (100%); 162 (85%).

Example 88

N-(4.5-Dihydro-1H-imidazol-2-ylmethyl)-2-(2-methyl-1.3-oxazol-4-yl)aniline hydrochloride 2-Bromo-2'-nitroacetopenone (1.55 g, 6.92 mmol) was dissolved in acetic acid (10 mL) under a nitrogen atmosphere. Potassium acetate (1.36 g, 13.84 mmol) was added, and the solution heated to reflux for two hours. The mixture was cooled to room temperature and ammonium acetate (1.87 g, 24.22 mmol) was added. The mixture was heated to reflux and maintained for three hours. After cooling, the mixture was poured into ice water, and carefully neutralized with 10N sodium hydroxide solution. The product was extracted with ethyl acetate (3×25 mL). The extracts were combined, washed with saturated sodium chloride solution, dried over magnesium sulfate, and the volatiles were removed by evaporation under reduced pressure to yield 1.3 g of crude 2-methyl-4-(2-nitrophenyl)oxazole, which was reduced as in Example 64 and purified by silica gel chromatography to give 0.075 g of 4-(2-aminophenyl)-2-methyloxazole.

4-(2-Aminophenyl)-2-methyloxazole (0.073 g, 0.42 mmol) and CMI (0.062 g, 0.39 mmol) were coupled under conditions described in the general procedure for CMI couplings to yield 0.040 g of N-(4,5-dihydro-1H-imidazol-2-ylmethyl)-2-(2-methyl-1,3-oxazol-4-yl)aniline as the hydrochloride salt.

Example 89

N-(4.5-Dihydro-1H-imidazol-2-ylmethyl)-2-(3-methyl-5-isoxazolyl)aniline fumarate 2-(3-Methyl-5-isoxazolyl)benzenamine (243 mg, 1.4 mmol, prepared as described by Sakamoto: *Tetrahedron*, 1991, 47, 5111–5118) and CMI (120 mg, 0.7 mmol) were coupled under conditions described in the general procedure for CMI couplings to give 121 mg of N-(4,5-dihydro-1H-imidazol-2-ylmethyl)-2-(3-methyl-5-isoxazolyl)aniline as the fumarate salt.

Example 90

N-(4.5-Dihydro(1H-imidazol-2-ylmethyl)-2-[1-(2.2.2-trifluoroethyl)1H-1.2.4-triazol-5-yl]aniline fumarate 2-Nitrobenzamide (2.5 g, 15 mmol) was dissolved in dimethylformamide-dimethylacetal (10 mL) and heated to 100° C. for 1 hour. Upon cooling, the reaction mixture was placed in a freezer at −23° C. overnight. The white precipitate was collected by filtration and rinsed with hexane to provide N-[(dimethylamino)methylene]-2-nitrobenzamide (3.06 g), which was used without further purification.

N-[(Dimethylamino)methylene]-2-nitrobenzamide (1.0 g, 4.5 mmol) in acetic acid (25 mL) and n-butanol (15 mL) was treated with 70% aqueous 1,1,1-trifluoroethylhydrazine (1 mL, 11.3 mmol), and heated to reflux for 2 hours, at which time the volume was reduced by ~25 mL by distillation. The remaining solvent was removed in vacuo, and the residue chromatographed on silica eluting with 3:1–1:1 hexane:ethyl acetate to afford 1-(2,2,2-trifluoroethyl)-5-(2-nitrophenyl)-1,2,4-triazole, which was reduced as in Example 64 to give crude 1-(2,2,2-trifluoroethyl)-5-(2-aminophenyl)-1,2,4-triazole (430 mg).

1-(2,2,2-Trifluoroethyl)-5-(2-aminophenyl)-1,2,4-triazole and CMI were coupled using conditions described in the general procedure for CMI coupling to give the fumaric acid salt of N-(4,5-dihydro-1H-imidazol-2-ylmethyl)-2-[1-(2,2,2-trifluoroethyl)-1H-1,2,4-triazol-5-yl]aniline.

$^1$H NMR (300 MHz, DMSO-$d_6$) δ 8.27 (s, 1H); 7.41 (dd, J=7.6 Hz, 7.6 Hz, 1H); 7.26 (d, J=7.4 Hz, 1H); 6.84 (dd, J=7.3 Hz, 7.3 Hz, 1H); 6.46 (s, 2H); 6.16 (t, J=5.5 Hz, 1H); 5.11 (q, J=8.9 Hz, 2H); 4.11 (d, J=5.5 Hz, 2H); 3.69 (s, 4H). Mass. Spec. 325 (100%) (M+H).

Example 91

N-(4,5-Dihydro-1H-imidazol-2-ylmethyl)-2-(1-isopropyl-1H-1,2,4-triazol-5-yl)aniline fumarate 1-tert-Butoxycarbonylhydrazine (10 g, 80 mmol) was dissolved in acetone (150 mL) and stirred overnight. Concentration in vacuo gave N-methylethylidene-N-tertutoxycarbonylhydrazine, which was used without further purification.

1-Methylethylidene-2-tert-butoxycarbonylhydrazine, glacial acetic acid (150 mL) and 10% palladium on carbon (2.0 g) were placed in a 500 mL Parr flask. The bottle was placed on a Parr apparatus, and after evacuating and flushing the bottle with nitrogen three times, the flask was charged with hydrogen to 40 psi. After hydrogen uptake ceased, the flask was evacuated and flushed with nitrogen. Filtration through celite, eluting with ethyl acetate, and concentration afforded the crude 1-(isopropyl)-2-tert-butoxycarbonylhydrazine as an acetic acid salt.

1-(isopropyl)-2-tert-butoxycarbonylhydrazine acetate (3.2 g, 18.4 mmol) was dissolved in methanol (35 mL) and treated with 4M hydrochloric acid in dioxane (10 mL). The reaction was stirred at room temperature for 24 hours, then heated to reflux for an additional 24 hours. Filtration through silica and concentration gave isopropylhydrazine as the hydrochloride salt.

N-[(Dimethylamino)methylene]-2-nitrobenzamide, prepared in Example 90, and isopropylhydrazine hydrochloric acid salt were reacted as in Example 90 to give 1-(2-propyl)-5-(2-nitrophenyl)-1,2,4-triazole, which was reduced and coupled with CMI similarly to give the fumaric acid salt of N-(4,5-dihydro-1H-imidazol-2-ylmethyl)-2-(2-propyl-1H-1,2,4-triazol-5-yl)aniline.

$^1$H NMR (300 MHz, DMSO-d$_6$) δ 8.15 (s, 1H); 7.39 (dd, J=7.8 Hz, 7.8 Hz, 1H); 7.24 (d, J=7.0 Hz, 1H); 6.85 (dd. J=7.4 Hz, 1H); 6.75 (d, J=8.4 Hz, 1H); 6.46 (s, 2H); 6.14 (t, J=5.3 Hz, 1H); 4.55 (m, J=6.4 Hz, 1H); 4.13 (d, J=5.3 Hz, 2H); 3.68 (s, 4H); 1.41 (d, J=6.5 Hz). Mass. Spec. 285 (95%) (M+H); 215 (100%) (M+H)–70).

Example 92

N-(4,5-Dihydro-1H-imidazol-2-ylmethyl)-2-(1-propyl-1H-1,2,4-triazol-5-yl)aniline fumarate In a fashion analogous to Example 90, 1-(1-propyl)-5-(2-nitrophenyl)-1,2,4-triazole was prepared, the nitro reduced, and the resulting 1-(1-propyl)-5-(2-aminophenyl)-1,2,4-triazole coupled with CMI to give the fumaric acid salt of N-(4,5-dihydro-1H-imidazol-2-ylmethyl)-2-(1-propyl-1H-1,2,4-triazol-5-yl)aniline.

Example 93

N-(4,5-Dihydro-1H-imidazol-2-ylmethyl)-2-(1-butyl-1H-1,2,4-triazol-5-yl)aniline fumarate In a fashion analogous to Example 90, 1-(1-butyl)-5-(2-nitrophenyl)-1,2,4-triazole was prepared, the nitro reduced, and the resulting 1-(1-butyl)-5-(2-aminophenyl)-1,2,4-triazole coupled with CMI to give the fumaric acid salt of N-(4,5-dihydro-1H-imidazol-2-ylmethyl)-2-(1-butyl-1H-1,2,4-triazol-5-yl)aniline.

Example 94

N-(4,5-Dihydro-1H-imidazol-2-ylmethyl)-2-(1-ethyl-1H-1,2,4-triazol-5-yl)aniline fumarate In a fashion analogous to Example 90, 1-ethyl-5-(2-nitrophenyl)-1,2,4-triazole was prepared, the nitro reduced, and the resulting 1-ethyl-5-(2-aminophenyl)-1,2,4-triazole coupled with CMI to give the fumaric acid salt of N-(4,5-dihydro-1H-imidazol-2-ylmethyl)-2-(1-ethyl-1H-1,2,4-triazol-5-yl)aniline.

Example 95

N-(4,5-Dihydro-1H-imidazol-2-ylmethyl)-2-(1-methyl-1H-1,2,4-triazol-5-yl)aniline In a fashion analogous to Example 90, 1-methyl-5-(2-nitrophenyl)-1,2,4-triazole was prepared, the nitro reduced, and the resulting 1-methyl-5-(2-aminophenyl)-1,2,4-triazole coupled with CMI to give N-(4,5-dihydro-1H-imidazol-2-ylmethyl)-2-(1-methyl-1H-1,2,4-triazol-5-yl)aniline.

Example 96

N-(4,5-Dihydro-1H-imidazol-2-ylmethyl)-2-(1H-1,2,4-triazol-5-yl)aniline hydrochloride In a fashion analogous to Example 90, 1-H-5-(2-nitrophenyl)-1,2,4-triazole was prepared, the nitro reduced, and the resulting 1-H-5-(2-aminophenyl)-1,2,4-triazole coupled with CMI to give the hydrochloric acid salt of N-(4,5-dihydro-1H-imidazol-2-ylmethyl)-2-(1-butyl-1H-1,2,4-triazol-5-yl)aniline.

Example 97

N-(4,5-Dihydro-1H-imidazol-2-ylmethyl)-2-(1H-pyrrol-1-yl)aniline fumarate

CMI (91%) (0.35 g, 2.05 mmol) and 1-(2-aminophenyl)pyrrole (0.60 g, 3.8 mmol, 2.0 eq) were coupled under conditions described in the general procedure for CMI coupling to give 0.13 g of N-(4,5-dihydro-1H-imidazol-2-ylmethyl)-2-(1H-pyrrol-1-yl)aniline fumarate.

Example 98

N-(4,5-Dihydro-1H-imidazol-2-ylmethyl)-2(2,5-dimethyl-1H-pyrrol-1-yl)aniline fumarate Acetonylacetone (2.0 g, 17.5 mmol), o-nitroaniline (2.6 g, 18.8 mmol, 1.07 eq), and p-toluenesulfonic acid monohydrate (0.31 g, 1.63 mmol) in toluene (75 mL) were heated at reflux with azeotropic removal of water overnight. The crude product was purified by column chromatography over silica gel to give 2.28 g of 2,5-dimethyl-1-(2-nitrophenyl)-1H-pyrrole, which was reduced as in Example 64 to give 0.46 g of 2-(2,5-dimethyl-1H-pyrrol-1-yl)benzenamine.

CMI (91%) (0.343 g, 2.0 mmol) and 2-(2,5-dimethyl-1H-pyrrol-1-yl)benzenamine (0.458 g, 2.46 mmol, 1.2 eq) were coupled as described in the general procedure for CMI coupling to give 0.033 g of N-(4,5-dihydro-1H-imidazol-2-ylmethyl)-2-(2,5-dimethyl-1H-pyrrol-1-yl)aniline fumarate.

Example 99

N-(4,5-Dihydro-1H-imidazol-2-ylmethyl)-2-(2-oxazolyl)aniline fumarate 2-(2-Nitrophenyl)oxazole was made by the process reported by Cass as modified by Jung [Cass, W. E.; J.Amer.Chem.Soc. 1942, 64, 785; Jung, Michael E.; Dansereau, Susan M. K.; Heterocycles, 1994, 39, (2), 767–78.], and reduced under conditions similar to Example 64 to give 2-(2-aminophenyl)oxazole.

CMI and 2-(2-aminophenyl)-oxazole were coupled using conditions described in the general procedure for CMI coupling to furnish the fumarate salt of N-(4,5-dihydro-1H-imidazol-2-ylmethyl)-2-(2-oxazolyl)aniline.

Example 100

N-(4,5-Dihydro-1H-imidazol-2-ylmethyl)-2-(1H-pyrazol-4-yl)aniline fumarate

3-Dimethylamino-2-(2-nitrophenyl)propenal (Maybridge) in ethanol was treated with hydrazine via syringe and heated to reflux for 16 hours. Concentration in vacuo afforded crude 4-(2-nitrophenyl)pyrazole, which was reduced as in Example 64 and coupled with CMI to give the fumaric acid salt of N-(4,5-dihydro-1H-imidazol-2-ylmethyl)-2-(1H-pyrazol-4-yl)aniline.

Example 101

N-(4,5-Dihydro-1H-imidazol-2-ylmethyl)-2-(1-methyl-1H-pyrazol-5-yl)aniline fumarate 3-(Dimethylamino)-2'-nitroacrylophenone (3.0 g, 13.5 mmol) in absolute ethanol (25 mL) was treated with methylhydrazine (800 μL, 20 mmol) and heated to reflux for 5 hours. The solvent was distilled off, and the residue chromatographed on silica eluting with 2:1 hexane:ethyl acetate to provide 1-methyl-5-(2-nitrophenyl)pyrazole (1.9 g) and 1-methyl-3-(2-nitrophenyl)pyrazole (350 mg).

1-Methyl-5-(2-nitrophenyl)pyrazole was reduced as in Example 64 and coupled with CMI under conditions described in the general procedure for CMI coupling to give the fumaric acid salt of N-(4,5-dihydro-1H-imidazol-2-ylmethyl)-2-(1-methyl-1H-pyrazol-5-yl)aniline.

$^1$H NMR (300 MHz, DMSO-d$_6$) δ 7.51 (s, 1H); 7.26 (dd, J=7.6 Hz, 7.6 Hz, 1H); 7.08 (d, J=7.1 Hz, 1H); 6.76 (dd, J=7.4 Hz, 7.4 Hz, 1H); 6.62 (d, J=8.2 Hz, 1H); 6.42 (s, 2H); 6.37 (s, 1H); 5.33 (t, J=5.5 Hz, 1H); 4.19 (d, J=5.5 Hz, 2H); 3.69 (s, 4H); 3.63 (s, 3H). Mass. Spec. 256 (90%) (M+H); 186 (100%) (M+H−70).

Example 102

N-(4,5-Dihydro-1H-imidazol-2-ylmethyl)-2-(1-methyl-1H-pyrazol-3-yl)aniline methanesulfonate 1-Methyl-3-(2-nitrophenyl)pyrazole, prepared in Example 101, was reduced as in Example 64 and coupled with CMI under conditions described in the general procedure for CMI coupling to give the methanesulfonic acid salt of N-(4,5-dihydro-1H-imidazol-2-ylmethyl)-2-(1-methyl-1H-pyrazol-3-yl)aniline.

$^1$H NMR (400 MHz, DMSO-d$_6$) δ 9.97 (s, 2H); 8.06 (brs. 1H); 7.80 (d, J=2.2 Hz, 1H); 7.64 (d, J=7.1 Hz, 1H); 7.16 (dd, J=7.5 Hz, 7.5 Hz, 1H); 6.76 (m, 2H); 6.52 (d, J=8.0 Hz, 1H); 4.43 (s, 2H); 3.92 (s, 3H); 3.84 (s, 4H); 2.30 (s, 3H). Mass. Spec. 256 (10%) (M+H); 186 (40%) (M+H−70).

Example 103

N-(4,5-Dihydro-1H-imidazol-2-ylmethyl)-2-(1-ethyl-1H-pyrazol-5-yl)aniline fumarate As in Example 101, 1-ethyl-5-(2-nitrophenyl)pyrazole (630 mg) and 1-ethyl-3-(2-nitrophenyl)pyrazole (120 mg) were prepared and separated by chromatography.

1-Ethyl-5-(2-nitrophenyl)pyrazole, was reduced as in Example 64 and coupled with CMI under conditions described in the general procedure for CMI coupling to give the fumaric acid salt of N-(4,5-dihydro-1H-imidazol-2-ylmethyl)-2-(1-ethyl-1H-pyrazol-5-yl)aniline.

$^1$H NMR (300 MHz, DMSO-d$_6$) δ 7.53 (d, J=1.4 Hz, 1H); 7.26 (dd, J=7.6 Hz, 7.6 Hz, 1H); 7.05 (d, J=7.4 Hz, 1H); 6.76 (dd, J=7.4 Hz, 7.4 Hz, 1H); 6.63 (d, J=8.2 Hz, 1H); 6.42 (s, 2H); 6.34 (d, J=1.4 Hz, 1H); 5.25 (t, J=5.8 Hz, 1H); 4.09 (d, J=5.8 Hz, 2H); 3.89 (q, J=7.2 Hz, 2H); 3.69 (s, 4H); 1.21 (t, J=7.2 Hz, 3H). Mass. Spec. 270 (100%) (M+H); 200 (90%) (M+H−70).

Example 104

N-(4,5-Dihydro-1H-imidazol-2-ylmethyl)-2-(1-ethyl-1H-pyrazol-3-yl)aniline fumarate 1-Ethyl-3-(2-nitrophenyl)pyrazole, prepared in Example 103, was reduced as in Example 64 and coupled with CMI under conditions described in the general procedure for CMI coupling to give the fumaric acid salt of N-(4,5-dihydro-1H-imidazol-2-ylmethyl)-2-(1-ethyl-1H-pyrazol-3-yl)aniline.

$^1$H NMR (300 MHz, DMSO-d$_6$) δ 8.06(t, J=5.5 Hz, 1H); 7.81 (d, J=2.2 Hz, 1H); 7.58 (d, J=7.1 Hz, 1H); 7.12 (dd, J=7.5 Hz, 7.5 Hz, 1H); 6.69 (m, 2H); 6.54 (d, J=8.3 Hz, 1H); 6.41 (s, 2H); 4.25 (d, J=5.3 Hz, 2H); 4.18 (q, J=7.3 Hz, 2H); 3.70 (s, 4H); 1.43 (t, J=7.3 Hz, 3H). Mass. Spec. 270 (30%) (M+H); 200 (100%) (M+H−70).

Example 105

N-(4,5-Dihydro-1H-imidazol-2-ylmethyl)-2-[1-(2,2,2-trifluoroethyl)-1H-pyrazol-5-yl]aniline fumarate As in Example 101, 1-(2,2,2-trifluoroethyl)-5-(2-nitrophenyl)pyrazole was prepared and purified by chromatography. The nitro group was reduced as in Example 64 and the product coupled with CMI under conditions described in the general procedure for CMI coupling to give the fumaric acid salt of N-(4,5-dihydro-1H-imidazol-2-ylmethyl)-2-[1-(2,2,2-trifluoroethyl)-1H-pyrazol-5-yl]aniline.

Example 106

N-(4,5-Dihydro-1H-imidazol-2-ylmethyl)-2-(1H-pyrazol-3-yl)aniline

As in Example 101, 3-(2-nitrophenyl)pyrazole (900 mg) was prepared. It was reduced as in Example 64 and coupled with CMI under conditions described in the general procedure for CMI coupling to give N-(4,5-dihydro-1H-imidazol-2-ylmethyl)-2-(1H-pyrazol-3-yl)aniline.

Example 107

4-{2-[(4,5-Dihydro-1H-imidazol-2-ylmethyl)amino]phenyl}-2-pyrimidinamine hydrochloride 3-(dimethylamino)2'-nitroacrylophenone (1.0 g, 4.54 mmol) in absolute ethanol (25 mL) was treated with guanidine hydrochloride (540 mg, 5.68 mmol), and 10N sodium hydroxide (200 µL). The reaction was heated to reflux for 18 hours. Upon cooling a white precipitate was collected by filtration and rinsed with diethyl ether to give 4-(2-nitrophenyl)-2-pyrimidineamine (400 mg). Additional material was obtained by concentration and chromatography on silica, eluting with 1;1 hexane:ethyl acetate.

4-(2-Nitrophenyl)-2-pyrimidineamine was reduced as in Example 64 and coupled with CMI under conditions described in the general procedure for CMI coupling to give the hydrochloric acid salt of 4-{2-[(4,5-dihydro-1H-imidazol-2-ylmethyl)amino]phenyl}-2-pyrimidinamine.

Example 108

N-(4,5-Dihydro-1H-imidazol-2-ylmethyl)-2-(5-isoxazolyl)aniline hydrochloride 5-(2-nitrophenyl)isoxazole (850 mg, 4.5 mmol), prepared as in Example 101, was added portionwise to a suspension of stannous chloride dihydrate (3.3 g, 14.6 mmol) in concentrated hydrochloric acid (8.3 mL). The reaction was heated to 105° C. four 1 hour. The reaction was cooled to 10° C. and filtered, and the solid was added to water (10 mL). The solution was adjusted to pH 10 with 10N sodium hydroxide, and extracted with methylene chloride. The organic layer was dried over magnesium sulfate, filtered and concentrated in vacuo to give 5-(2-aminophenyl)isoxazole (220 mg), which was coupled with CMI under conditions described in the general procedure for CMI coupling to give the hydrochloric acid salt of N-(4,5-dihydro-1H-imidazol-2-ylmethyl)-2-(5-isoxazolyl)aniline.

Example 109

N-(4,5-Dihydro-1H-imidazol-2-ylmethyl)-2-(3-methyl-1,2,4-oxadiazol-5-yl)aniline

2-Nitrobenzamide (12.4 g, 75 mmol) was dissolved to dimethylacetamide-dimethylacetal (25 mL) and heated to 120° C. for 2 hours. Upon cooling, the reaction was passed through a short silica column, eluting with ethyl acetate. The crystals that formed in the collected eluent were collected by filtration and rinsed with diethyl ether to provide N-[(dimethylamino)ethylidene]-2-nitrobenzamide (7.73 g).

To a solution of hydroxylamine hydrochloride (1.37 g, 20.1 mmol) in 5N aqueous sodium hydroxide (3.9 mL) was added N-[(dimethylamino)ethylidene]-2-nitrobenzamide (3.7 g, 15.7 mmol) portionwise. After stirring 20 minutes, the reaction was diluted with water (30 mL) and placed in a −23° C. freezer for 1 hour. The yellow crystals were collected by filtration. This material was dissolved in glacial acetic acid and heated to 110° C. for 14 hours. Toluene (30 mL) was added and the reaction fitted with a Dean-Stark Trap. The toluene was removed by distillation over a 2 hour period, and after cooling, water was added to the reaction mixture. After 2 hours in a −23° C. freezer, the precipitate was collected by filtration and rinsed with water to give 3-methyl-5-(2-nitrophenyl)-1,2,4-oxadiazole (2.63 g).

3-methyl-5-(2-nitrophenyl)-1,2,4-oxadiazole (1.0 g, 4.8 mmol) in dioxane (11 mL) at 80°0 C. was treated with 11 mL of an aqueous solution of sodium sulfide nonahydrate (2.55 g, 10.6 mmol), also at 80° C. After stirring at that temperature for 45 minutes, the reaction was diluted with water (15 mL) and cooled in an ice bath. The resulting precipitate was collected by filtration and rinsed with water to afford 3-methyl-5-(2-aminophenyl)-1,2,4-oxadiazole (522 mg).

3-Methyl-5-(2-aminophenyl)-1,2,4-oxadiazole (250 mg, 1.43 mmol) and CMI (148 mg, 0.96 mmol) were dissolved in methanol (10 mL) and heated to 110° C. The methanol was allowed to boil off and the residue heated an additional 2 hours. Upon cooling to room temperature, the residue was chromatographed on basic alumina. eluting 1–5% methanol in methylene chloride, to afford N-(4,5-dihydro-1H-imidazol-2-ylmethyl)-2-(3-methyl-1,2,4-oxadiazol-5-yl) aniline (14 mg).

Example 110

N-(4,5-Dihydro-1H-imidazol-2-ylmethyl)-2-(1,3-dimethyl-1H-1,2,4-triazol-5-yl)aniline Under conditions similar to Example 90, using N-[(dimethylamino)ethylidene]-2-nitrobenzamide, prepared in Example 109, 1,3-dimethyl-5-(2-nitrophenyl)-1H-1,2,4-triazole was prepared.

1,3-Dimethyl-5-(2-nitrophenyl)-1H-1,2,4-triazole (0.80 g, 3.67 mmol) was reduced as in Example 64 and coupled with CMI under conditions described in the general procedure for CMI coupling to give N-(4,5-dihydro-1H-imidazol-2-ylmethyl)-2-(1,3-dimethyl-1H-1,2,4-triazol-5-yl)aniline.

Example 111

N-(4,5-Dihydro-1H-imidazol-2-ylmethyl)-2-(3-methyl-1H-1,2,4-triazol-5-yl)aniline hydrochloride As in Example 110, 3-methyl-5-(2-nitrophenyl)-1H-1,2,4-triazole was prepared. It was reduced as in Example 64 and coupled with CMI under conditions described in the general procedure for CMI coupling to give N-(4,5-dihydro-1H-imidazol-2-ylmethyl)-2-(3-methyl-1H-1,2,4-triazol-5-yl)aniline hydrochloride.

Example 112

N-(4,5-Dihydro-1H-imidazol-2-ylmethyl)-2-(5-methyl-1,2,4-oxadiazol-3-yl)aniline

Sodium wire (4.0 g, 173 mmol) was added slowly to anhydrous methanol (400 mL) and stirred for 15 minutes. To this solution was added hydroxylamine hydrochloride (10.0 g, 147 mmol), followed by 2-nitrobenzonitrile (10.0 g, 67.5 mmol). The reaction was heated to reflux for 18 hours, and then concentrated in vacuo. The residue was dissolved in water and extracted with chloroform several times. After concentration, the material was dissolved in methanol and diethyl ether then diluted with hexane until the solution became cloudy. After 5 hours at 0° C., the crystals were collected by filtration and rinsed with hexane to give 1-N-hydroxy-2-(2-nitrophenyl)amidine (6.14 g).

1-N-Hydroxy-2-(2-nitrophenyl)amidine (1.0 g, 5.52 mmol) in acetic anhydride (15 mL) was heated to 120° C. for 16 hours. Concentration and chromatography on silica, eluting with 2:1 hexane;ethyl acetate gave 3-(2-nitrophenyl)-5-methyl-1,2,4-oxadiazole.

3-(2-Nitrophenyl)-5-methyl-1,2,4-oxadiazole was reduced and coupled with CMI as in Example 109 to give N-(4,5-dihydro-1H-imidazol-2-ylmethyl)-2-(5-methyl-1,2,4-oxadiazol-3-yl)aniline.

Example 113

N-(4,5-Dihydro-1H-imidazol-2-ylmethyl)-2-(1,3-oxazol-5-aniline hydrochloride 5-(2-Nitrophenyl)oxazole was reduced as in Example 64 and coupled with CMI under conditions described in the general procedure for CMI coupling to give the hydrochloric acid salt of N-(4,5-dihydro-1H-imidazol-2-ylmethyl)-2-(1,3-oxazol-5-yl)aniline.

$^1$H NMR (300 MHz, DMSO-$d_6$ δ 10.03 (s, 2H); 8.47 (s, 1H); 7.59 (s, 1H); 7.48 (d, J=7.6 Hz, 1H); 7.26 (dd, J=7.7 Hz, 7.7 Hz, 1H); 6.83 (dd, J=7.5 Hz, 7.5 Hz, 1H); 6.60 (d, J=8.1 Hz, 1H); 5.91 (t, J=5.6 Hz, 1H); 4.29 (d, J=5.5 Hz, 2H); 3.82 (s, 4H). Mass. Spec. 243 (98%) (M+H); 173 (100%) (M+H−70).

Example 114

N-[5-Chloro-2-(1,3-oxazol-5-yl)phenyl]-N-(4,5-dihydro-1H-imidazol-2-ylmethyl)amine fumarate To a solution of 2-nitro-4-chlorobenzaldehyde (2.2 g, 11.8 mmol) and p-toluenesulfonyl-methylisocyanide (2.8 g, 14.2 mmol) in methanol (50 mL) was added potassium carbonate (8.2 g, 59 mmol) solid. The heterogeneous mixture was heated to reflux for 2.5 hours. Upon moving to room temperature, the reaction was filtered and concentrated in vacuo. The residue was dissolved in 0.1N sodium hydroxide and extracted with methylene chloride two times. The combined organics were dried over sodium sulfate, filtered and concentrated in vacuo to give crude 5-(2-nitro-4-chlorophenyl)oxazole.

5-(2-Nitro-4-chlorophenyl)oxazole was reduced as in Example 64 and coupled with CMI under conditions described in the general procedure for CMI coupling to give the fumarate salt of N-[5-chloro-2-(1,3-oxazol-5-yl)phenyl]-N-(4,5-dihydro-1H-imidazol-2-ylmethyl)amine.

Example 115

N-(4,5-Dihydro-1H-imidazol-2-ylmethyl)-2-(4-methyl-1,3-oxazol-5-yl)aniline fumarate To a 500-ml round bottom flask was added p-toluenesulfonylmethyl isocyanide (4.0 g, 20.5 mmol), iodomethane (5.8 g, 40.9 mmol, 2.0 eq), benzyltriethylammonium chloride (1.1 g, 4.4 mmol, 0.2 eq) and dichloromethane (40 mL). The solution was cooled in an ice-water bath. To the cold solution was added a cold solution of 30% sodium hydroxide (40 mL). The reaction mixture was stirred vigorously at 0° C. for 3 h. To the reaction mixture was added dichloromethane and the layers were separated. The aqueous phase was extracted with dichloromethane. The organic solutions were combined, dried over magnesium sulfate, filtered and concentrated in vacuo to give an oil. The oil was extracted with cold diethyl ether. The diethyl ether solution was filtered and the filtrate was concentrated in vacuo to give 3.6 g of 1-[(1-isocyanotethyl)sulfonyl]-4-methylbenzene.

Using conditions similar to Example 114, with 1-[(1-isocyanotethyl)sulfonyl]-4-methylbenzene and 2-nitrobenzaldehyde, 4-methyl-5-(2-nitrophenyl)-1,3-oxazole was prepared. This was reduced as in Example 64 and coupled with CMI under conditions described in the general procedure for CMI coupling to give N-(4,5-dihydro-1H-imidazol-2-ylmethyl)-2-(4-methyl-1,3-oxazol-5-yl) aniline fumarate.

Example 116

N-(4,5-Dihydro-1H-imidazol-2-ylmethyl)-2-(1-isopropyl-1H-pyrazol-5-yl)aniline fumarate 1-Isopropyl-5-(2-nitrophenyl)pyrazole (prepared from isopropylhydrazine and 3-(dimethylamino)-2'-nitroacrylophenone using the method described in Example 101), was reduced as in Example 64 and coupled with CMI under conditions described in the general procedure for CMI coupling to give the fumaric acid salt of N-(4,5-dihydro-1H-imidazol-2-ylmethyl)-2-(1-isopropyl-1H-pyrazol-5-yl) aniline.

Example 117

N-(4,5-Dihydro-1H-imidazol-2-ylmethyl)-2-(1-ethyl-1H-pyrazol-4-yl)aniline fumarate 1-Ethyl-4-(2-nitrophenyl)pyrazole (prepared from ethylhydrazine and 3-dimethylamino-2-(2-nitrophenyl)propenal using the method described in Example 100), was reduced as in Example 64 and coupled with CMI under conditions described in the general procedure for CMI coupling to give the fumaric acid salt of N-(4,5-dihydro-1H-imidazol-2-ylmethyl)-2-(1-ethyl-1H-pyrazol-4-yl)aniline.

Example 118

N-(4,5-Dihydro-1H-imidazol-2-ylmethyl)-2-(1-methyl-1H-pyrazol-4-yl)aniline fumarate 1-Methyl-4-(2-nitrophenyl)pyrazole (prepared from methylhydrazine and 3-dimethylamino-2-(2-nitrophenyl) propenal using the method described in Example 100), was reduced as in Example 64 and coupled with CMI under conditions described in the general procedure for CMI coupling to give the fumaric acid salt of N-(4,5-dihydro-1H-imidazol-2-ylmethyl)-2-(1-methyl-1H-pyrazol-4-yl) aniline.

Example 119

{2-[(4,5-Dihydro-1H-imidazol-2-ylmethyl)amino]-6-methylphenyl}(1-pyrrolidinyl)methanone 5-Methyl-2H-3,1-benzoxazine-2,4(1H)-dione was prepared from 2-amino-6-methylbenzoic acid using the method described in Example 38.

{2-Amino-6-methylphenyl}(1-pyrrolidinyl)methanone (prepared from pyrrolidine and 5-methyl-2H-3,1-benzoxazine-2,4(1H)-dione using the methods described in Example 17) and CMI were reacted using conditions described in the general procedure for CMI coupling to give {2-[(4,5-dihydro-1H-imidazol-2-ylmethyl)amino]-6-methylphenyl}(1-pyrrolidinyl)methanone.

Example 120

{5-Bromo-2-[(4,5-dihydro-1H-imidazol-2-ylmethyl) amino]phenyl}(1-pyrrolidinyl)methanone 6-Bromo-2H-3,1-benzoxazine-2,4(1H)-dione was prepared from 2-amino-5-bromobenzoic acid using the method described in Example 38.

{2-amino-5-bromophenyl}(1-pyrrolidinyl)methanone (prepared from pyrrolidine and 6-bromo-2H-3,1-benzoxazine-2,4(1H)-dione using the methods described in Example 17) and CMI were reacted using conditions described in the general procedure for CMI coupling to give {5-bromo-2-[(4,5-dihydro-1H-imidazol-2-ylmethyl)amino] phenyl}(1-pyrrolidinyl)methanone.

Example 121

{5-Bromo-2-[(4,5-dihydro-1H-imidazol-2-ylmethyl) amino]-3-methylphenyl}(1-pyrrolidinyl)methanone 6-Bromo-8-methyl-2H-3,1-benzoxazine-2,4(1H)-dione was prepared from 2-amino-5-bromo-3-methylbenzoic acid using the method described in Example 38.

{2-Amino-5-bromo-3-methylphenyl}(1-pyrrolidinyl) methanone (prepared from pyrrolidine and 6-bromo-8-methyl-2H-3,1-benzoxazine-2,4-(1H)-dione using the methods described in Example 17) and CMI were reacted using conditions described in the general procedure for CMI coupling to give {5-bromo-2-[(4,5-dihydro-1H-imidazol-2-ylmethyl)amino]-3-methylphenyl}(1-pyrrolidinyl) methanone.

Example 122

{5-Chloro-2-[(4,5-dihydro-1H-imidazol-2-ylmethyl) amino]phenyl}(1-pyrrolidinyl)methanone 6-Chloro-2H-3,1-benzoxazine-2,4(1H)-dione was prepared from 2-amino-5-chlorobenzoic acid using the method described in Example 38.

{2-Amino-5-chlorophenyl}(1-pyrrolidinyl)methanone (prepared from pyrrolidine and 6-chloro-2H-3,1-benzoxazine-2,4(1H)-dione using the methods described in Example 17) and CMI were reacted using conditions described in the general procedure for CMI coupling to give {5-chloro-2-[(4,5-dihydro-1H-imidazol-2-ylmethyl)amino] phenyl}(1-pyrrolidinyl)methanone.

Example 123

1-{2-[(4,5-Dihydro-1H-imidazol-2-ylmethyl)amino]-4,5-dimethoxyphenyl}-1-ethanone hydrochloride 1-(2-Amino-4,5-dimethoxyphenyl)ethanone and were reacted using conditions described in the general procedure for CMI coupling to 1-{2-[(4,5-Dihydro-1H-imidazol-2-ylmethyl)amino]-4,5-dimethoxyphenyl}-1-ethanone as the hydrochloride salt.

Example 124

N-(4,5-Dihydro-1H-imidazol-2-ylmethyl)-5-chloro-2-(methylsulfonyl)aniline fumarate Starting from 5-chloro-2-methylbenzothiazole, N-(4,5-Dihydro-1H-imidazol-2-ylmethyl)-5-chloro-2-

(methylsulfonyl)aniline fumarate was prepared and isolated using the procedures described in Example 8.

$^1$H NMR (300 MHz, DMSO-d$_6$): δ 3.21 (s, 3H), 3.66 (s, 4H), 4.22 (br d, J=5.2 Hz, 2H), 6.51 (s, 2H), 6.89 (m, 3H), 7.65 (d, J=9.0 Hz, 1H), Mass. Spec. 288 (100%) (M+H).

Functional assay for agonist activity at cloned human Alpha$_1$ Adrenoceptors

Agonist activity of compounds at alpha$_{1A}$, alpha$_{1B}$, and alpha$_{1D}$ adrenoceptors was examined using flourescent dye determination of intracellular free calcium concentrations. Rat-1 fibroblast cells expressing human alpha$_{1A}$, alpha$_{1B}$, and alpha$_{1D}$ adrenoceptor subtypes, were grown in DMEM, 10% fetal calf serum, and 0.25 mg/ml G418. Cells released from 225 cm$^2$ cell culture flasks with trypsin were diluted in the above media and added to 96 well clear bottom culture plates and grown for 48 hours at 37° C. and 5% CO$_2$. Cells were washed in a buffer comprised of 145 mM NaCl, 5 mM KCl, 0.5 mM CaCl$_2$, 1 mM MgCl$_2$, 10 mM HEPES, 10 mM glucose, pH 7.4 (assay buffer) to remove the growth media. Cells were loaded with Calcium Green dye (2 mM stock in DMSO, mixed 50/50 with 20% pluronic acid) at a 2 μM final concentration in the assay buffer containing 2.5 mM probeneacid by incubation in the presence of dye for one hour at 37° C. After incubation, the plates were allowed to come to room temperature, washed twice with 100 μl assay buffer, and brought to a final assay volume of 50 μl.

Basal intracellular calcium concentrations were monitored for 10 seconds before adding the unknown with an integrated 96 well pipettor. Fluorescence was measured from all 96 wells simultaneously using a CCD camera. Agonist activity was measured every second for the first 25 seconds then every 3 seconds for the next 15 seconds. Agonist efficacy was expressed as a percentage of the maximal response to phenylephrine. As used herein, an "agonist" is a compound that elicits a maximal response greater than 50% of that of phenylephrine, with a pEC$_{50}$>5.5. The compounds in Examples 1–115 and Example 124 all are alpha-1A agonists.

What is claimed is:
1. A compound of formula (I) or a pharmaceutically acceptable salt or solvate thereof,

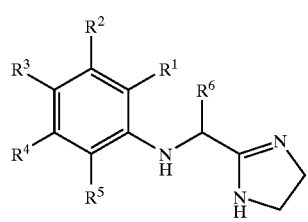

(I)

wherein R$^2$, R$^3$, R$^4$, and R$^5$ are independently H, halogen, —OH, —C$_{1-3}$alkyl, —C$_{1-3}$alkoxy, —SC$_{1-2}$alkyl, or —CF$_3$, with the proviso that at least 2 of R$^2$, R$^3$, R$^4$, and R$^5$ are H;

R$^6$ is H or —CH$_3$;
R$^1$ is —S(O)$_n$R$^7$ where n is 1 or 2, —S(O)$_2$NHR$^8$, —C(O)R$^9$, —NR$^{14}$R$^{15}$, —C(R$^{17}$)=NOR$^{16}$,

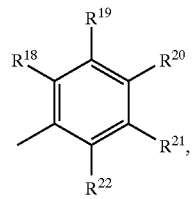

or a 5, 6, or 7 membered heteroalkyl or heteroaryl group optionally substituted with 1 or two groups selected from the group consisting of the following substituents for carbon: C$_{1-3}$alkyl, —CH$_2$CF$_3$, —CF$_3$, F, Cl, C$_{1-2}$alkoxy, C$_{1-2}$thioalkyl, and the following substituents for nitrogen: C$_{1-3}$alkyl and —CH$_2$C$_{1-2}$fluoroalkyl;

R$^7$ is C$_{1-3}$alkyl or C$_{1-2}$fluoroalkyl;
R$^8$ is C$_{1-3}$alkyl or —CH$_2$C$_{1-2}$fluoroalkyl;
R$^9$ is C$_{1-3}$alkyl optionally substituted with 1–3 fluorine atoms, —NR$^{10}$R$^{11}$, —NHNR$^{12}$R$^{13}$, —CH$_2$SO$_2$CH$_3$,

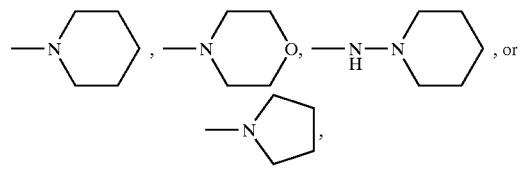

R$^{10}$ is H or C$_{1-2}$alkyl;
R$^{11}$ is H, cyclopropyl, cyclopropylmethyl, C$_{3-6}$alkenyl with the proviso that any unsaturation is not adjacent to the depicted nitrogen, or C$_{1-6}$alkyl optionally substituted with hydroxy, C$_{1-3}$alkoxy, or 1–3 fluorine atoms with the proviso that the carbon atom in R$^{11}$ that is bonded to the depicted nitrogen is not bonded to either a fluorine or an oxygen;
R$^{12}$ is H or C$_{1-2}$alkyl;
R$^{13}$ is H, C$_{3-5}$cycloalkyl, cyclopropylmethyl, —SO$_2$CH$_3$, —C(O)CH$_3$, C$_{3-6}$alkenyl with the proviso that any unsaturation is not adjacent to the depicted nitrogen, or C$_{1-6}$alkyl optionally substituted with hydroxy, C$_{1-3}$alkoxy, or 1–3 fluorine atoms with the proviso that the carbon atom in R$^{13}$ that is bonded to the depicted nitrogen is not bonded to either a fluorine or an oxygen;
R$^{14}$ is H or C$_{1-2}$alkyl;
R$^{15}$ is C$_{3-5}$cycloalkyl, cyclopropylmethyl, C$_{3-6}$alkenyl with the proviso that any unsaturation is not adjacent to the depicted nitrogen, or C$_{1-6}$alkyl optionally substituted with hydroxy, C$_{1-3}$alkoxy, or 1–3 fluorine atoms with the proviso that the carbon atom in R$^{15}$ that is bonded to the depicted nitrogen is not bonded to either a fluorine or an oxygen;
R$^{16}$ is C$_{1-2}$alkyl;
R$^{17}$ is H or C$_{1-3}$alkyl;
R$^{20}$ is H; and
R$^{18}$, R$^{19}$, R$^{21}$, and R$^{22}$ are independently H, halogen, hydroxy, C$_{1-3}$alkyl, C$_{1-3}$alkoxy, —SC$_{1-2}$alkyl, or —CF$_3$ with the proviso that at least one of R$^{18}$, R$^{19}$, R$^{21}$, or R$^{22}$ is other than H.

2. A compound of claim 1 wherein R$^2$, R$^3$, and R$^5$ are H or F.

3. A compound of claim 2 wherein R$^4$=H, F, Cl, —OCH$_3$, or —CH$_3$.

4. A compound of claim 3 wherein R$^6$ is H.

5. A compound of claim 4 wherein R$^1$ is —S(O)nR$^7$, S(O)$_2$NHR$^8$,

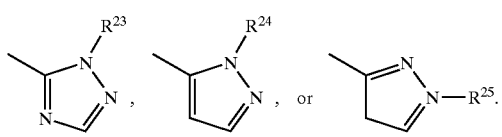

where $R^{23}$ is H, $C_{1-3}$alkyl, or 2,2,2-trifluoroethyl, $R^{24}$ is H, $C_{1-3}$alkyl, or 2,2,2-trifluoroethyl, and $R^{25}$ is H, methyl, or ethyl.

6. A compound of claim 5 where $R^1$ is

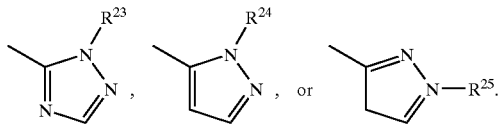

where $R^{23}$ is isopropyl or 2,2,2-trifluoromethyl, $R^{24}$ is methyl or ethyl, and $R^{25}$ is methyl, or ethyl.

7. A compound of claim 5 wherein $R^1$ $S(O)_2NHR^8$.
8. A compound of claim 7 wherein $R^8$ is $CH_3$.
9. A compound of claim 5 wherein $R^1$ is $-S(O)nR^7$.
10. A compound of claim 9 wherein n is 2 and $R^7$ is $CH_3$.
11. A compound of claim 1 selected from the group consisting of
2-[(4,5-dihydro-1H-imidazol-2-ylmethyl)amino]-N-propylbenzamide,
N-cyclopropyl-2-[(4,5-dihydro-1H-imidazol-2-ylmethyl)amino]benzamide,
2-[(4,5-dihydro-1H-imidazol-2-ylmethyl)amino]-N-methylbenzamide,
{2-[(4,5-dihydro-1H-imidazol-2-ylmethyl)amino]phenyl}(4-morpholinyl)methanone,
2-[(4,5-dihydro-1H-imidazol-2-ylmethyl)amino]-N,N-diethylbenzamide,
2-[(4,5-dihydro-1H-imidazol-2-ylmethyl)amino]-N-ethyl-N-methylbenzamide,
2-[(4,5-dihydro-1H-imidazol-2-ylmethyl)amino]-N-methyl-N-propylbenzamide,
N-(4,5-dihydro-1H-imidazol-2-ylmethyl)-2-(1,3-oxazol-5-yl)aniline,
1-{2-[(4,5-dihydro-1H-imidazol-2-ylmethyl)amino]phenyl}-1-ethanone,
N-(4,5-dihdyro-1H-imidazol-2-ylmethyl)-2-(2-pyrazinyl)aniline,
N-(4,5-dihydro-1H-imidazol-2-ylmethyl)-2-(2-methyl-1,3-thiazol-4-yl)aniline,
N-(4,5-dihydro-1H-imidazol-2-ylmethyl)-2-(1-methyl-1H-pyrazol-3-yl)aniline,
N-(4,5-dihydro-1H-imidazol-2-ylmethyl)-2-(1-methyl-1H-pyrazol-5-yl)aniline,
N-(4,5-dihydro-1H-imidazol-2-ylmethyl)-2-(methylsulfonyl)aniline,
2-[(4,5-dihydro-1H-imidazol-2-ylmethyl)amino]-N-methylbenzenesulfonamide,
N-(4,5-dihydro-1H-imidazol-2-ylmethyl)-2-(1-methyl-1H-pyrrol-2-yl)aniline,
N-(4,5-dihydro-1H-imidazol-2-ylmethyl)-2-(1-ethyl-1H-pyrazol-3-yl)aniline,
N-(4,5-dihydro-1H-imidazol-2-ylmethyl)-2-(1-ethyl-1H-pyrazol-5-yl)aniline,
2-[(4,5-dihydro-1H-imidazol-2-ylmethyl)amino]-N-ethylbenzenesulfonamide,
N-(4,5-dihydro-1H-imidazol-2-ylmethyl)-2-(1-ethyl-1H-pyrrol-2-yl)aniline,
N-(4,5-dihydro-1H-imidazol-2-ylmethyl)-2-[1-(2,2,2-trifluoroethyl)-1H-1,2,4-triazol-5-yl]aniline,
N-(4,5-dihydro-1H-imidazol-2-ylmethyl)-2-(ethylsulfonyl)aniline,
N-(4,5-dihydro-1H-imidazol-2-ylmethyl)-5-fluoro-2-(methylsulfonyl)aniline,
N-(4,5-dihydro-1H-imidazol-2-ylmethyl)-5-chloro-2-(methylsulfonyl)aniline,
N-(4,5-dihydro-1H-imidazol-2-ylmethyl)-5-methyl-2-(methylsulfonyl)aniline,
N-(4,5-dihydro-1H-imidazol-2-ylmethyl)-5-methoxy-2-(methylsufonyl)aniline,
N-(4,5-dihydro-1H-imidazol-2-ylmethyl)-2-[1-isopropyl-1H-1,2,4-triazol-5-yl]aniline, and pharmaceutically acceptable salts and solvates thereof.

12. A compound of claim 1 selected from the group consisting of
N-(4,5-dihydro-1H-imidazol-2-ylmethyl)-5-fluoro-2-(methylsulfonyl)aniline,
N-(4,5-dihydro-1H-imidazol-2-ylmethyl)-2-(1-ethyl-1H-pyrazol-5-yl)aniline,
2-[(4,5-dihydro-1H-imidazol-2-ylmethyl)amino]-N-methylbenzenesulfonamide,
N-(4,5-dihydro-1H-imidazol-2-ylmethyl)-2-[1-(2,2,2-trifluoroethyl)-1H-1,2,4-triazol-5-yl]aniline,
N-(4,5-dihydro-1H-imidazol-2-ylmethyl)-2-(methylsulfonyl)aniline, and pharmaceutically acceptable salts and solvates thereof.

13. A compound of claim 1 selected from the group consisting of N-(4,5-dihydro-1H-imidazol-2-ylmethyl)-2-(methylsulfonyl)aniline and pharmaceutically acceptable salts and solvates thereof.

14. A pharmaceutical composition comprising a therapeutically effective amount of a compound of claim 1.

15. A pharmaceutical composition according to claim 14 further comprising a pharmaceutically acceptable diluent or carrier.

16. A process for preparing a compound as claimed in claim 1 which comprises reacting a compound of formula II:

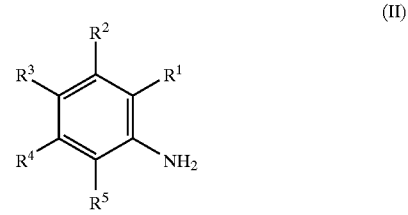

with a compound of formula III:

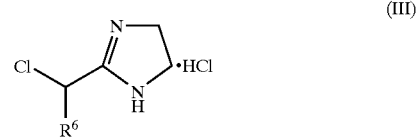

17. A process as claimed in claim 16 wherein the reaction is carried out at a pH in the range of from 3.0 to 4.0.

18. A process as claimed in claim 17 wherein the reaction is run in a protic solvent.

19. A process as claimed in claim 18 wherein said protic solvent is selected from the group consisting of methanol, ethanol, methoxyethanol, isopropanol, butanol, and phenol.

20. A process as claimed in claim 19 wherein the protic solvent is 2-butanol.

21. A process as claimed in claim 20 wherein the reaction is run at a temperature or temperatures of from 80 to 140° C.

* * * * *

UNITED STATES PATENT AND TRADEMARK OFFICE
CERTIFICATE OF CORRECTION

PATENT NO. : 6,884,801 B1
DATED : April 26, 2005
INVENTOR(S) : Bigham et al.

It is certified that error appears in the above-identified patent and that said Letters Patent is hereby corrected as shown below:

<u>Title page,</u>
Item [56], References Cited, FOREIGN PATENT DOCUMENTS, reads
"WO 0 887 346 12/1998" should read -- EP 0 887 346 12/1998 --

Signed and Sealed this

Ninth Day of August, 2005

JON W. DUDAS
*Director of the United States Patent and Trademark Office*